US012758249B2

(12) United States Patent
King et al.

(10) Patent No.: US 12,758,249 B2
(45) Date of Patent: Oct. 13, 2026

(54) SURGICAL INSTRUMENT WITH CLAMP ARM AND PIVOT SHAFT HINGE COUPLING

(71) Applicant: Cilag GmbH International, Zug (CH)

(72) Inventors: Jonathan D. King, Cincinnati, OH (US); Geoffrey S. Strobl, Williamsburg, OH (US); Barry C. Worrell, Maineville, OH (US)

(73) Assignee: CILAG GMBH INTERNATIONAL, Zug (CH)

( * ) Notice: Subject to any disclaimer, the term of this patent is extended or adjusted under 35 U.S.C. 154(b) by 107 days.

(21) Appl. No.: 18/415,216

(22) Filed: Jan. 17, 2024

(65) Prior Publication Data

US 2025/0025200 A1 Jan. 23, 2025

Related U.S. Application Data

(60) Provisional application No. 63/514,011, filed on Jul. 17, 2023.

(51) Int. Cl.
*A61B 17/32* (2006.01)
*A61B 17/00* (2006.01)

(52) U.S. Cl.
CPC ................ *A61B 17/320092* (2013.01); *A61B 17/320068* (2013.01); *A61B 2017/00367* (2013.01);
(Continued)

(58) Field of Classification Search
CPC .... A61B 17/320092; A61B 17/320068; A61B 2017/00367; A61B 2017/00982;
(Continued)

(56) References Cited

U.S. PATENT DOCUMENTS

| | | | |
|---|---|---|---|
| 975,515 | A | 11/1910 | Davies |
| 1,852,542 | A | 4/1932 | Sovatkin |

(Continued)

FOREIGN PATENT DOCUMENTS

| | | | |
|---|---|---|---|
| AU | 2015258304 | A1 | 12/2015 |
| EP | 0214107 | A1 | 3/1987 |

(Continued)

OTHER PUBLICATIONS

International Search Report and Written Opinion dated Oct. 10, 2024, for International Application No. PCT/IB2024/056855, 15 pages.

(Continued)

*Primary Examiner* — Richard G Louis
(74) *Attorney, Agent, or Firm* — FBT Gibbons LLP

(57) ABSTRACT

A surgical instrument includes a body, a shaft assembly, an ultrasonic blade, and a clamp arm assembly. The shaft assembly extends distally from the body and includes an outer sheath and a first pivot portion such that the outer sheath and the first pivot portion are integrally formed together with each other as a first unitary piece. The clamp arm assembly includes a clamp arm and a second pivot portion such that the clamp arm and the second pivot portion are integrally formed together with each other as a second unitary piece. The clamp arm assembly is pivotally coupled to the shaft assembly via the first and second pivot portions.

20 Claims, 23 Drawing Sheets

(52) U.S. Cl.
CPC ............... *A61B 2017/00982* (2013.01); *A61B 2017/320074* (2017.08); *A61B 2017/320082* (2017.08); *A61B 2017/320088* (2013.01); *A61B 2017/320094* (2017.08)

(58) Field of Classification Search
CPC ....... A61B 2017/320074; A61B 2017/320082; A61B 2017/320088; A61B 2017/320094; A61B 2017/2825; A61B 2017/320095; A61B 2090/0427; A61B 2090/0472; A61B 2090/08021; A61B 2090/0807
See application file for complete search history.

(56) References Cited

U.S. PATENT DOCUMENTS

| | | | | |
|---|---|---|---|---|
| 5,322,055 | A | 6/1994 | Davison et al. | |
| 5,792,135 | A | 8/1998 | Madhani et al. | |
| 5,817,084 | A | 10/1998 | Jensen | |
| 5,873,873 | A | 2/1999 | Smith et al. | |
| 5,878,193 | A | 3/1999 | Wang et al. | |
| 5,925,064 | A * | 7/1999 | Meyers | A61B 17/320016 606/205 |
| 5,980,510 | A | 11/1999 | Tsonton et al. | |
| 6,231,565 | B1 | 5/2001 | Tovey et al. | |
| 6,325,811 | B1 | 12/2001 | Messerly | |
| 6,361,317 | B1 | 3/2002 | Rahman | |
| 6,364,888 | B1 | 4/2002 | Niemeyer et al. | |
| 6,773,444 | B2 | 8/2004 | Messerly | |
| 6,783,524 | B2 | 8/2004 | Anderson et al. | |
| 7,524,320 | B2 | 4/2009 | Tierney et al. | |
| 7,691,098 | B2 | 4/2010 | Wallace et al. | |
| 7,806,891 | B2 | 10/2010 | Nowlin et al. | |
| 8,461,744 | B2 | 6/2013 | Wiener et al. | |
| 8,479,969 | B2 | 7/2013 | Shelton, IV | |
| 8,573,461 | B2 | 11/2013 | Shelton, IV et al. | |
| 8,573,465 | B2 | 11/2013 | Shelton, IV | |
| 8,591,536 | B2 | 11/2013 | Robertson | |
| 8,602,288 | B2 | 12/2013 | Shelton, IV et al. | |
| 8,616,431 | B2 | 12/2013 | Timm et al. | |
| 8,623,027 | B2 | 1/2014 | Price et al. | |
| 8,783,541 | B2 | 7/2014 | Shelton, IV et al. | |
| 8,800,838 | B2 | 8/2014 | Shelton, IV | |
| 8,820,605 | B2 | 9/2014 | Shelton, IV | |
| 8,844,789 | B2 | 9/2014 | Shelton, IV et al. | |
| 8,986,302 | B2 | 3/2015 | Aldridge et al. | |
| 9,023,071 | B2 | 5/2015 | Miller et al. | |
| 9,095,367 | B2 | 8/2015 | Olson et al. | |
| 9,301,759 | B2 | 4/2016 | Spivey et al. | |
| 9,381,058 | B2 | 7/2016 | Houser et al. | |
| 9,393,037 | B2 | 7/2016 | Olson et al. | |
| 9,888,934 | B2 | 2/2018 | Storz et al. | |
| 10,172,636 | B2 | 1/2019 | Stulen et al. | |
| 10,258,363 | B2 | 4/2019 | Worrell et al. | |
| 10,952,759 | B2 | 3/2021 | Messerly et al. | |
| 11,020,200 | B2 | 6/2021 | Boudreaux et al. | |
| 11,051,835 | B2 | 7/2021 | Schulte et al. | |
| 11,116,532 | B2 | 9/2021 | Asher et al. | |
| 11,324,527 | B2 | 5/2022 | Aldridge et al. | |
| 2003/0050634 | A1* | 3/2003 | Ellman | A61B 18/12 606/49 |
| 2006/0079874 | A1 | 4/2006 | Faller et al. | |
| 2007/0191713 | A1 | 8/2007 | Eichmann et al. | |
| 2007/0198005 | A1* | 8/2007 | Ichihashi | A61B 17/320092 606/27 |
| 2007/0282333 | A1 | 12/2007 | Fortson et al. | |
| 2008/0200940 | A1 | 8/2008 | Eichmann et al. | |
| 2009/0099582 | A1 | 4/2009 | Isaacs et al. | |
| 2010/0256623 | A1* | 10/2010 | Nicolas | A61B 18/04 606/27 |
| 2010/0274160 | A1* | 10/2010 | Yachi | H01H 13/08 606/1 |
| 2010/0331873 | A1 | 12/2010 | Dannaher et al. | |
| 2012/0116265 | A1 | 5/2012 | Houser et al. | |
| 2013/0110155 | A1 | 5/2013 | Tsuchiya et al. | |
| 2013/0116717 | A1* | 5/2013 | Balek | A61N 7/00 606/169 |
| 2013/0303949 | A1 | 11/2013 | Kawaguchi et al. | |
| 2014/0257318 | A1 | 9/2014 | Behymer et al. | |
| 2015/0080925 | A1* | 3/2015 | Schulte | A61B 17/285 606/169 |
| 2018/0098809 | A1 | 4/2018 | Miyazaki | |
| 2020/0375619 | A1 | 12/2020 | Denzinger et al. | |
| 2023/0200839 | A1 | 6/2023 | Kase | |

FOREIGN PATENT DOCUMENTS

| | | | |
|---|---|---|---|
| GB | 924741 | A | 5/1963 |
| JP | 2004-033565 | A | 2/2004 |
| JP | 2005-176905 | A | 7/2005 |

OTHER PUBLICATIONS

International Search Report and Written Opinion dated Nov. 18, 2024, for International Application No. PCT/IB2024/056856, 18 pages.

International Search Report and Written Opinion dated Sep. 23, 2024, for International Application No. PCT/IB2024/056858, 12 pages.

International Search Report and Written Opinion dated Feb. 20, 2025, for International Application No. PCT/IB2024/056860, 22 pages.

U.S. Appl. No. 18/594,534, filed Mar. 4, 2024, by Worrell et al., entitled: "Clamp Arm of Surgical Instrument With Adjustable Coupling Stability and Related Methods."

U.S. Appl. No. 18/415,073, filed Jan. 17, 2024, by Dannaher, entitled: "Surgical Instrument With Integrated Tissue Stop."

U.S. Appl. No. 18/415,133, filed Jan. 17, 2024, by Dannaher et al., entitled: "Surgical Instrument With Elastomeric Distal Pipe and Related Methods."

U.S. Appl. No. 61/410,603, filed Nov. 5, 2010, by Houser, entitled: "Energy-Based Surgical Instruments."

U.S. Appl. No. 63/514,011, filed Jul. 17, 2023, by Burkart et al., entitled: "Methods of End Effector Assembly and Related Arrangements for Surgical Instruments."

* cited by examiner

SURGICAL INSTRUMENT WITH CLAMP ARM AND PIVOT SHAFT HINGE COUPLING

PRIORITY

This application claims priority to U.S. Provisional Pat. App. No. 63/514,011, entitled "Methods of End Effector Assembly and Related Arrangements for Surgical Instruments," filed Jul. 17, 2023, the entirety of which is hereby incorporated by reference herein.

BACKGROUND

A variety of surgical instruments include an end effector having a blade element that vibrates at ultrasonic frequencies to cut and/or seal tissue (e.g., by denaturing proteins in tissue cells). These instruments include piezoelectric elements that convert electrical power into ultrasonic vibrations, which are communicated along an acoustic waveguide to the blade element. The precision of cutting and coagulation may be controlled by the surgeon's technique and adjusting the power level, blade edge, tissue traction and blade pressure.

Examples of ultrasonic surgical instruments include the HARMONIC ACE® Ultrasonic Shears, the HARMONIC WAVER Ultrasonic Shears, the HARMONIC FOCUS® Ultrasonic Shears, and the HARMONIC SYNERGY® Ultrasonic Blades, all by Ethicon Endo-Surgery, Inc. of Cincinnati, Ohio. Further examples of such devices and related concepts are disclosed in U.S. Pat. No. 5,322,055, entitled "Clamp Coagulator/Cutting System for Ultrasonic Surgical Instruments," issued Jun. 21, 1994, the disclosure of which is incorporated by reference herein; U.S. Pat. No. 5,873,873, entitled "Ultrasonic Clamp Coagulator Apparatus Having Improved Clamp Mechanism," issued Feb. 23, 1999, the disclosure of which is incorporated by reference herein; U.S. Pat. No. 5,980,510, entitled "Ultrasonic Clamp Coagulator Apparatus Having Improved Clamp Arm Pivot Mount," filed Oct. 10, 1997, the disclosure of which is incorporated by reference herein; U.S. Pat. No. 6,325,811, entitled "Blades with Functional Balance Asymmetries for use with Ultrasonic Surgical Instruments," issued Dec. 4, 2001, the disclosure of which is incorporated by reference herein; U.S. Pat. No. 6,773,444, entitled "Blades with Functional Balance Asymmetries for Use with Ultrasonic Surgical Instruments," issued Aug. 10, 2004, the disclosure of which is incorporated by reference herein; and U.S. Pat. No. 6,783,524, entitled "Robotic Surgical Tool with Ultrasound Cauterizing and Cutting Instrument," issued Aug. 31, 2004, the disclosure of which is incorporated by reference herein.

Still further examples of ultrasonic surgical instruments are disclosed in U.S. Pub. No. 2006/0079874, entitled "Tissue Pad for Use with an Ultrasonic Surgical Instrument," published Apr. 13, 2006, the disclosure of which is incorporated by reference herein; U.S. Pub. No. 2007/0191713, entitled "Ultrasonic Device for Cutting and Coagulating," published Aug. 16, 2007, the disclosure of which is incorporated by reference herein; U.S. Pub. No. 2007/0282333, entitled "Ultrasonic Waveguide and Blade," published Dec. 6, 2007, the disclosure of which is incorporated by reference herein; U.S. Pub. No. 2008/0200940, entitled "Ultrasonic Device for Cutting and Coagulating," published Aug. 21, 2008, the disclosure of which is incorporated by reference herein; U.S. Pub. No. 2009/0105750, entitled "Ergonomic Surgical Instruments," published Apr. 23, 2009, the disclosure of which is incorporated by reference herein; U.S. Pub. No. 2010/0069940, entitled "Ultrasonic Device for Fingertip Control," published Mar. 18, 2010, the disclosure of which is incorporated by reference herein; and U.S. Pub. No. 2011/0015660, entitled "Rotating Transducer Mount for Ultrasonic Surgical Instruments," published Jan. 20, 2011, the disclosure of which is incorporated by reference herein; and U.S. Pub. No. 2012/0029546, entitled "Ultrasonic Surgical Instrument Blades," published Feb. 2, 2012, the disclosure of which is incorporated by reference herein.

Some of ultrasonic surgical instruments may include a cordless transducer such as that disclosed in U.S. Pub. No. 2012/0112687, entitled "Recharge System for Medical Devices," published May 10, 2012, the disclosure of which is incorporated by reference herein; U.S. Pub. No. 2012/0116265, entitled "Surgical Instrument with Charging Devices," published May 10, 2012, the disclosure of which is incorporated by reference herein; and/or U.S. Pat. App. No. 61/410,603, filed Nov. 5, 2010, entitled "Energy-Based Surgical Instruments," the disclosure of which is incorporated by reference herein.

Additionally, some ultrasonic surgical instruments may include an articulating shaft section. Examples of such ultrasonic surgical instruments are disclosed in U.S. Pub. No. 2014/0005701, entitled "Surgical Instruments with Articulating Shafts," published Jan. 2, 2014, the disclosure of which is incorporated by reference herein; and U.S. Pub. No. 2014/0114334, entitled "Flexible Harmonic Waveguides/Blades for Surgical Instruments," published Apr. 24, 2014 the disclosure of which is incorporated by reference herein.

While several surgical instruments and systems have been made and used, it is believed that no one prior to the inventors has made or used the invention described in the appended claims.

BRIEF DESCRIPTION OF THE DRAWINGS

While the specification concludes with claims which particularly point out and distinctly claim this technology, it is believed this technology will be better understood from the following description of certain examples taken in conjunction with the accompanying drawings, in which like reference numerals identify the same elements and in which:

Figure 1:
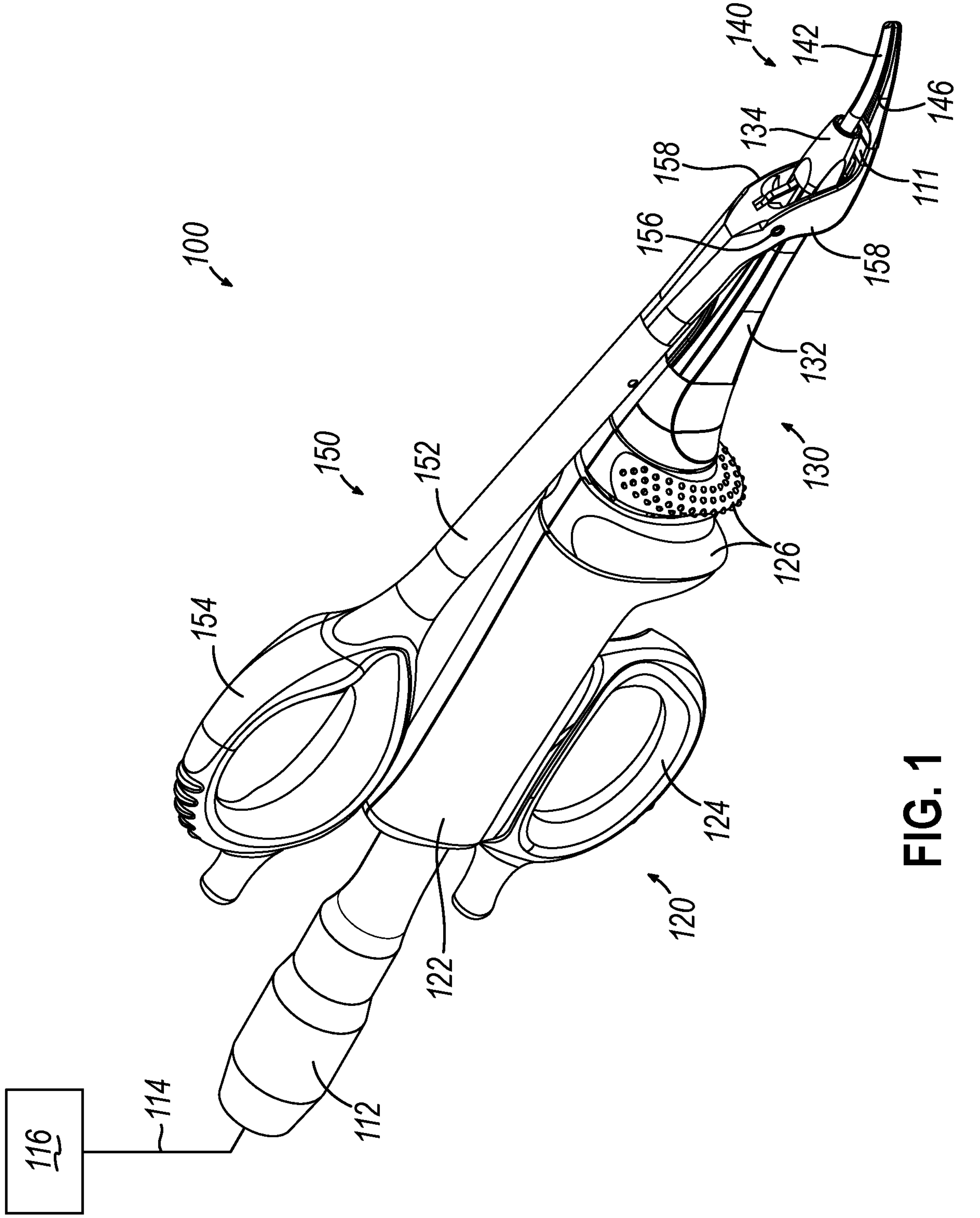
FIG. 1 depicts a perspective view of an exemplary surgical instrument.

The drawings are not intended to be limiting in any way, and it is contemplated that various embodiments of the technology may be carried out in a variety of other ways, including those not necessarily depicted in the drawings. The accompanying drawings incorporated in and forming a part of the specification illustrate several aspects of the present technology, and together with the description serve to explain the principles of the technology; it being understood, however, that this technology is not limited to the precise arrangements shown.

DETAILED DESCRIPTION

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

For clarity of disclosure, the terms "proximal" and "distal" are defined herein relative to a human or robotic operator of the surgical instrument. The term "proximal" refers the position of an element closer to the human or robotic operator of the surgical instrument and further away from the surgical end effector of the surgical instrument. The term "distal" refers to the position of an element closer to the surgical end effector of the surgical instrument and further away from the human or robotic operator of the surgical instrument.

I. Exemplary Ultrasonic Surgical Instrument

FIGS. 1-4 illustrate an exemplary ultrasonic surgical instrument (100). At least part of each instrument (100) may be constructed and operable in accordance with at least some of the teachings of U.S. Pat. Nos. 5,322,055; 5,873,873; 5,980,510; 6,325,811; 6,773,444; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2009/0105750; U.S. Pub. No. 2010/0069940; U.S. Pub. No. 2011/0015660; U.S. Pub. No. 2012/0112687; U.S. Pub. No. 2012/0116265; U.S. Pub. No. 2014/0005701; U.S. Pub. No. 2014/0114334; U.S. Pat. App. No. 61/410,603; and/or U.S. patent application Ser. No. 14/028,717. The disclosures of each of the foregoing patents, publications, and applications are incorporated by reference herein. As described therein and as will be described in greater detail below, instrument (100) is operable to cut tissue and seal or weld tissue (e.g., a blood vessel, etc.) substantially simultaneously. It should also be understood that instrument (100) may have various structural and functional similarities with the HARMONIC ACER Ultrasonic Shears, the HARMONIC WAVE® Ultrasonic Shears, the HARMONIC FOCUS® Ultrasonic Shears, and/or the HARMONIC SYNERGY® Ultrasonic Blades. Furthermore, instrument (100) may have various structural and functional similarities with the devices taught in any of the other references that are cited and incorporated by reference herein.

To the extent that there is some degree of overlap between the teachings of the references cited herein, the HARMONIC ACER Ultrasonic Shears, the HARMONIC WAVER Ultrasonic Shears, the HARMONIC FOCUS® Ultrasonic Shears, and/or the HARMONIC SYNERGY® Ultrasonic Blades, and the following teachings relating to instruments (100), there is no intent for any of the description herein to be presumed as admitted prior art. Several teachings herein will in fact go beyond the scope of the teachings of the references cited herein and the HARMONIC ACER Ultrasonic Shears, the HARMONIC WAVER Ultrasonic Shears, the HARMONIC FOCUS® Ultrasonic Shears, and the HARMONIC SYNERGY® Ultrasonic Blades.

FIG. 1 illustrates an exemplary ultrasonic surgical instrument (100) that is configured to be used in open surgical procedures. Instrument (100) of this example comprises a handle assembly (120), a shaft assembly (130), and an end effector (140). Handle assembly (120) comprises a body (122) including a finger grip ring (124) and a pair of buttons (126). Instrument (100) also includes a clamp arm assembly (150) that is pivotable toward and away from body (122). Clamp arm assembly (150) includes a shank (152) with a thumb grip ring (154). Thumb grip ring (154) and finger grip ring (124) together provide a scissor grip type of configuration. It should be understood, however, that various other suitable configurations may be used, including but not limited to a pistol grip configuration.

Figure 2:
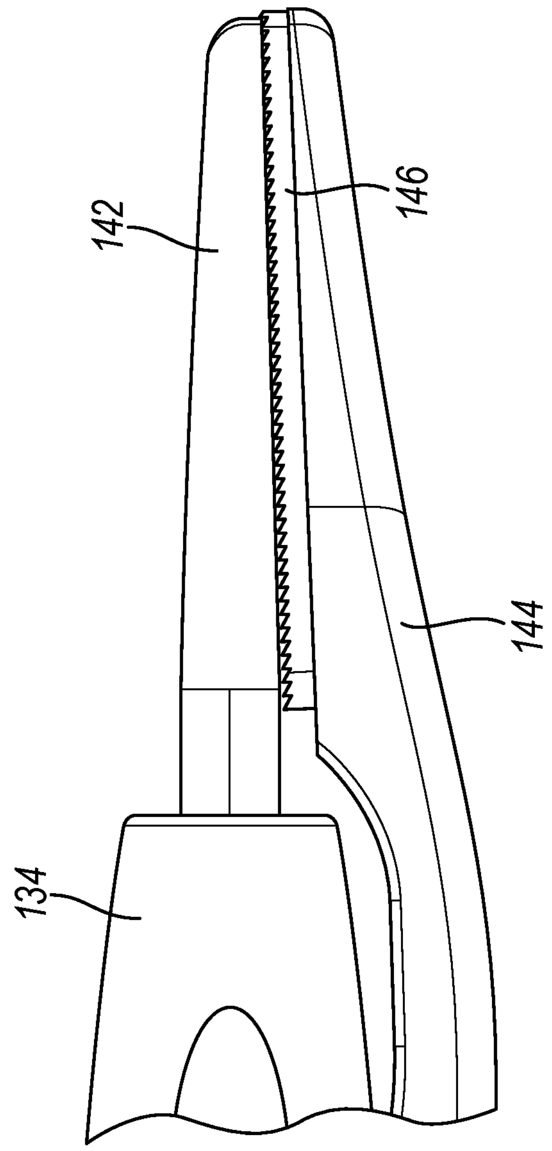
FIG. 2 depicts a side elevational view of the end effector of the instrument of FIG. 1, in a closed configuration.
Figure 3:
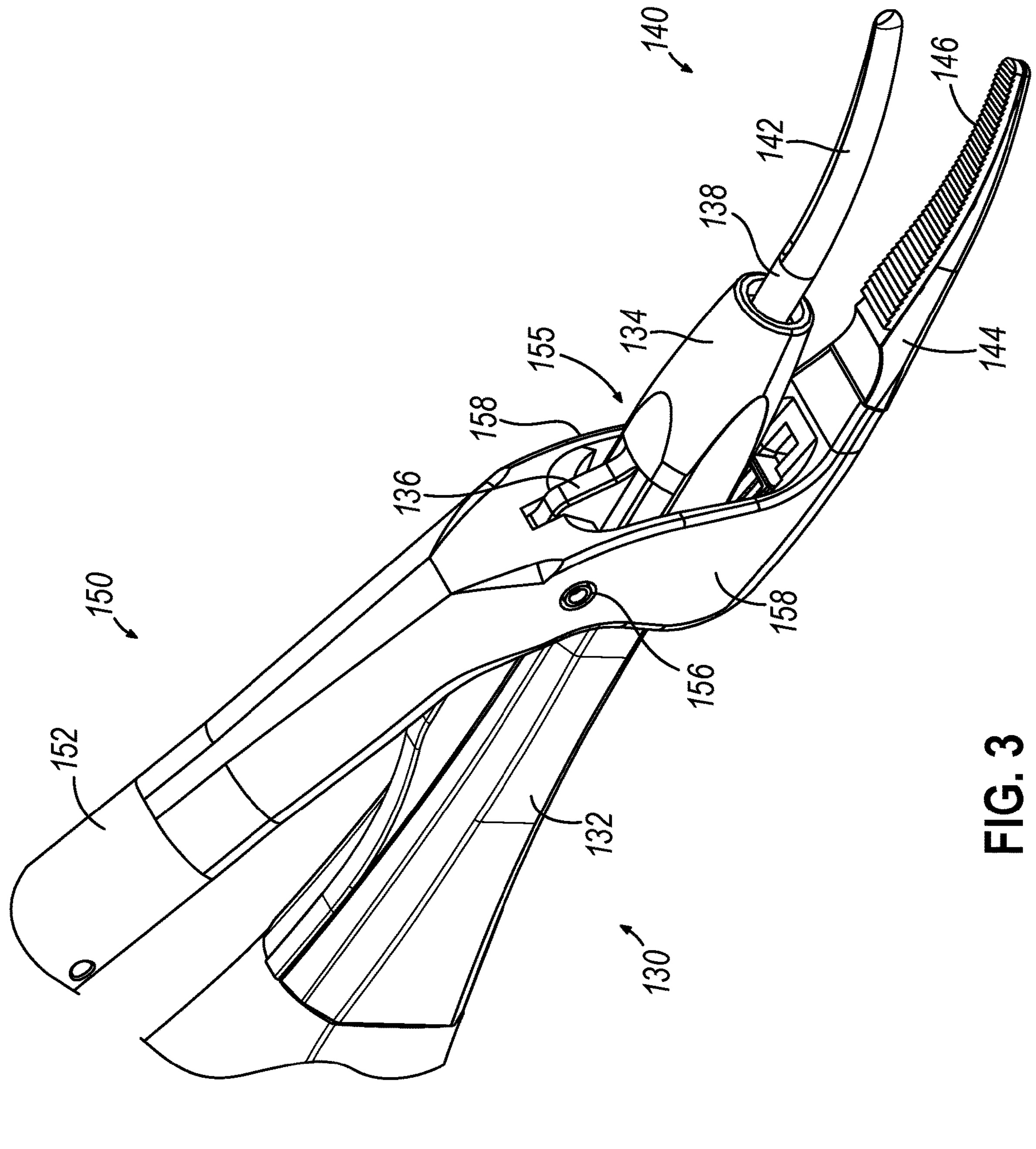
FIG. 3 depicts a perspective view of the end effector of FIG. 2, in an open configuration.
Figure 4:
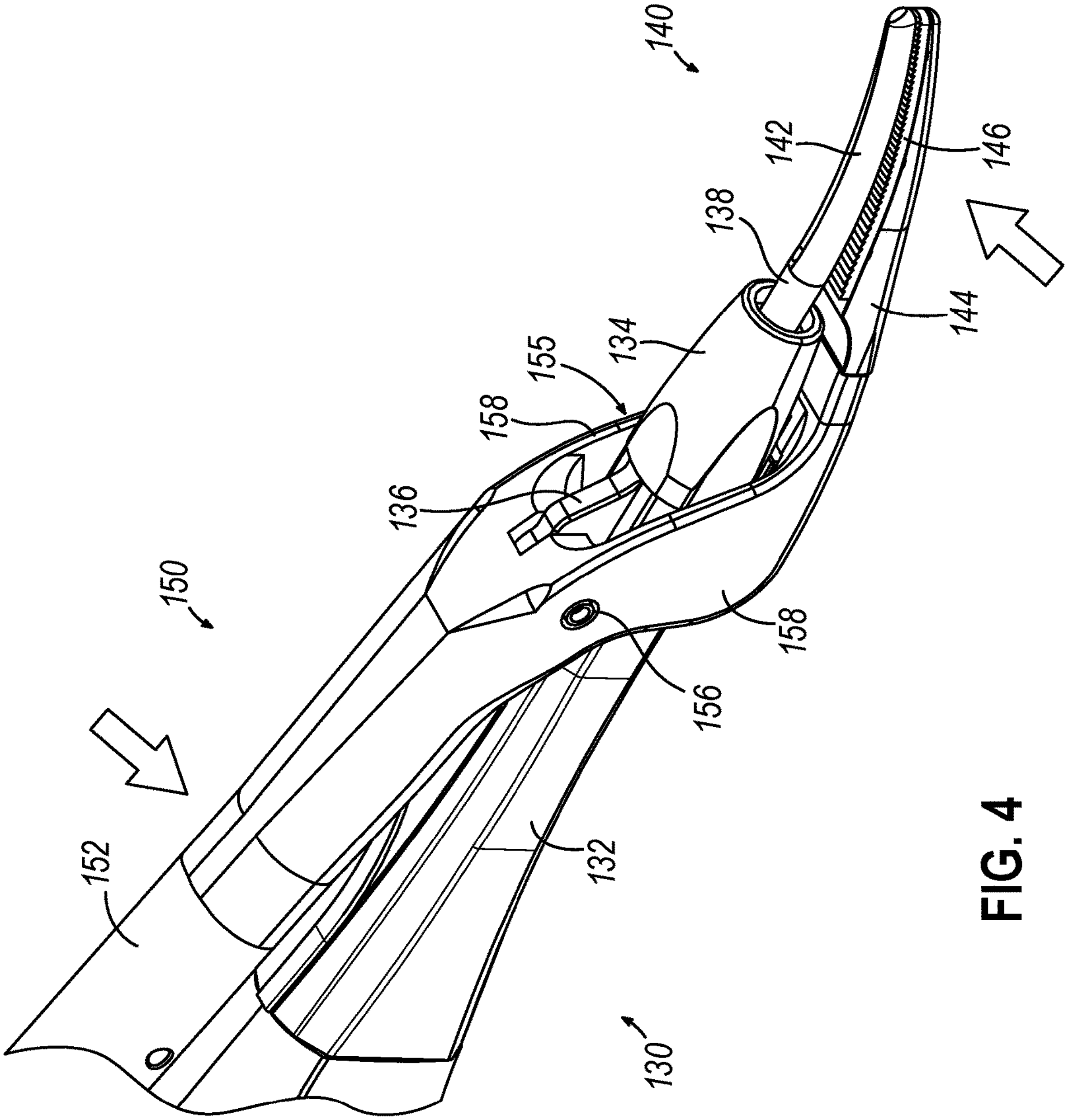
FIG. 4 depicts a perspective view of the end effector of FIG. 2, in a closed configuration.
Figure 5:
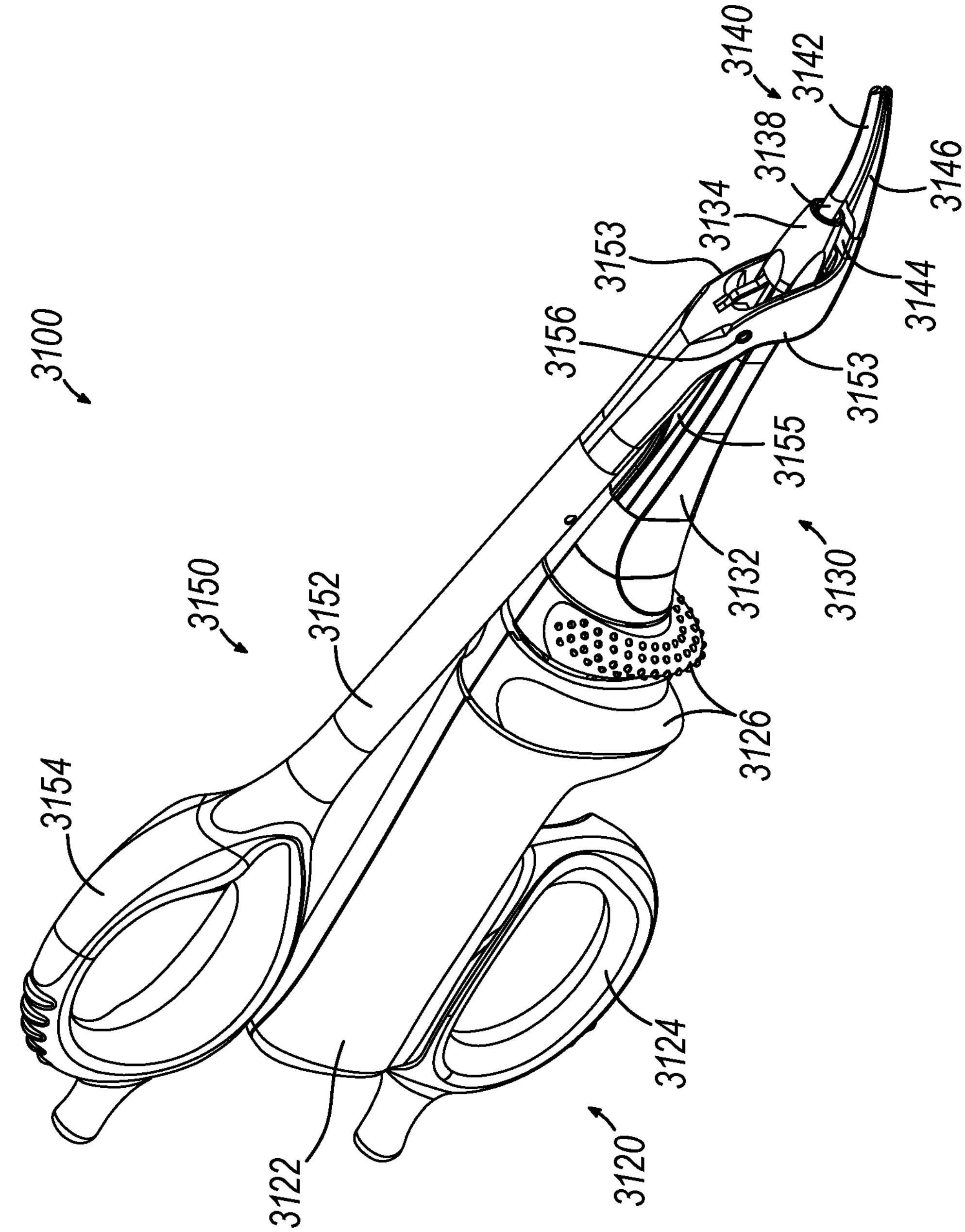
FIG. 5 depicts a perspective view of another example of a surgical instrument including a clamp arm assembly pivotally coupled to a shaft assembly, and having a pair of pivot bosses on the shaft assembly that are received within corresponding receptacles on the clamp arm assembly.
Figure 6:
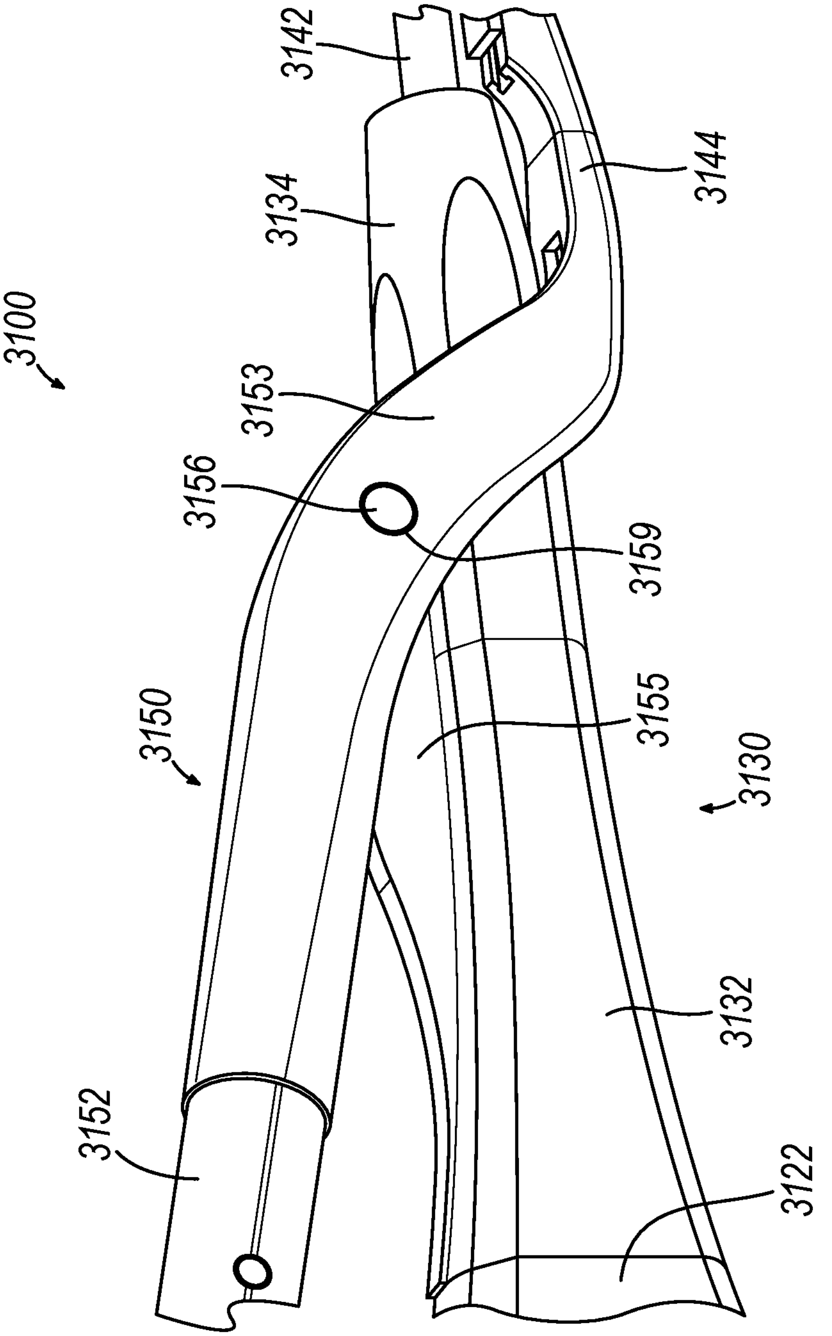
FIG. 6 depicts an enlarged perspective view of the surgical instrument of FIG. 5.
Figure 7:
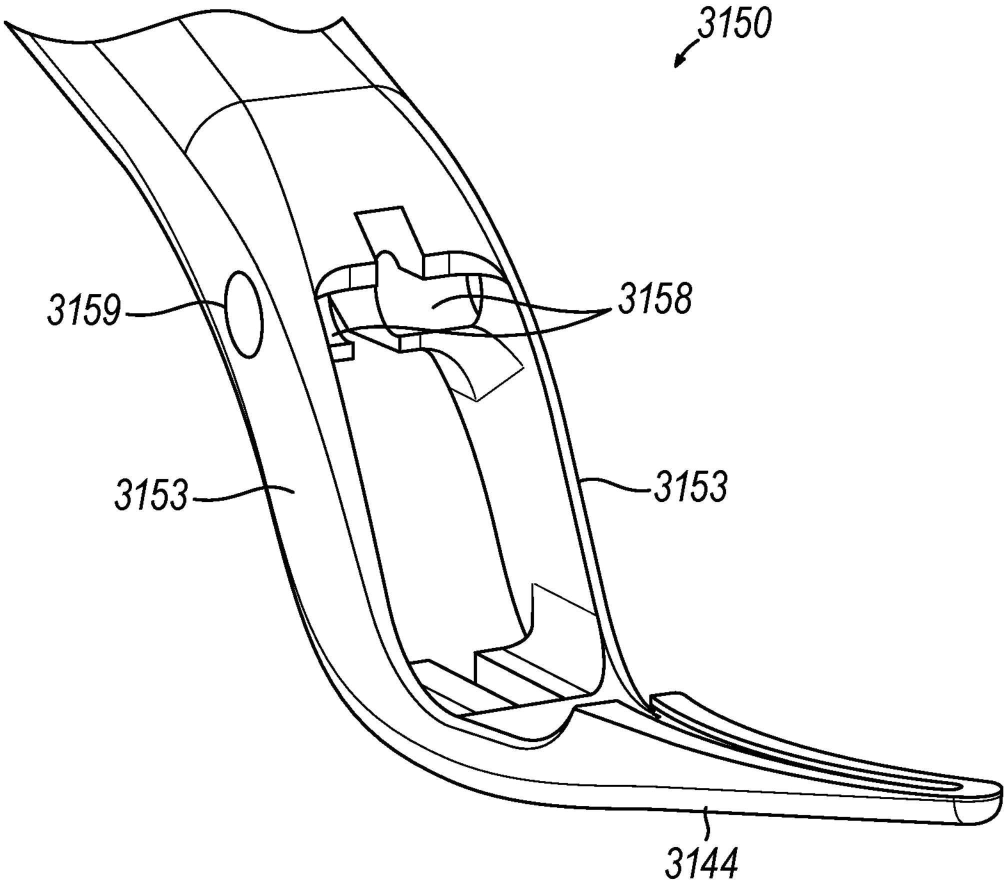
FIG. 7 depicts an enlarged perspective view of the clamp arm assembly of FIG. 5.
Figure 8:
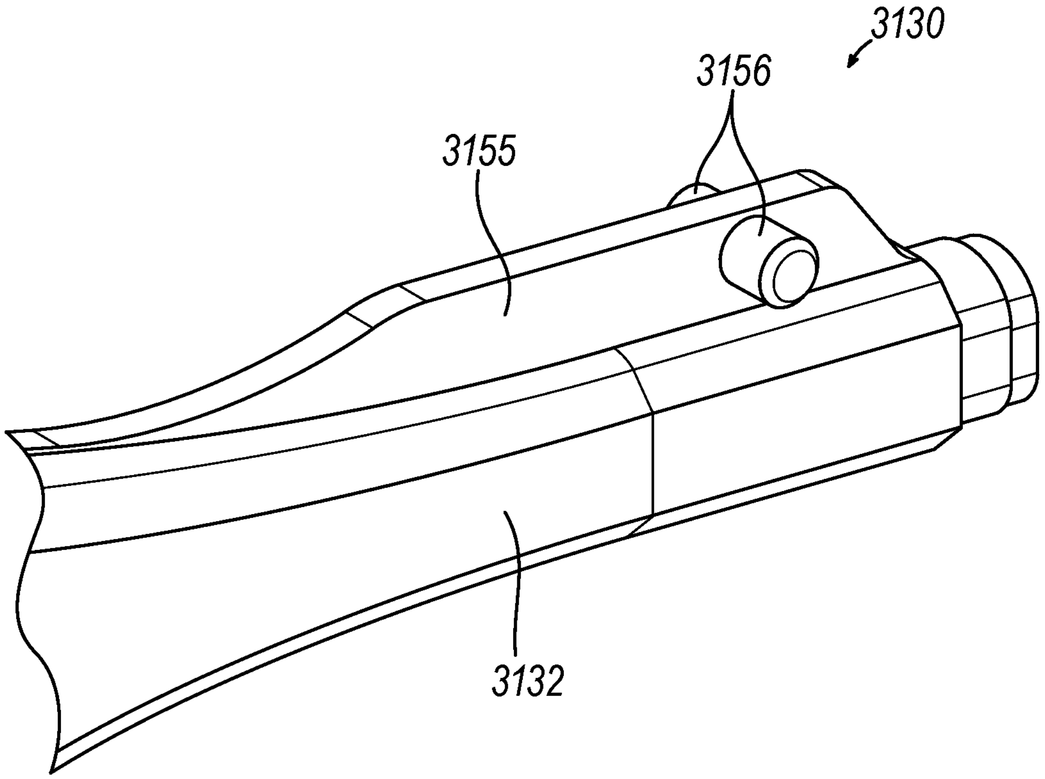
FIG. 8 depicts an enlarged perspective view of the shaft assembly of FIG. 5.

Shaft assembly (130) comprises an outer sheath (132) extending distally from body (122). A cap (134) is secured to the distal end of sheath (132). As best seen in FIGS. 2-4, end effector (140) comprises an ultrasonic blade (142) and a clamp arm (144). Ultrasonic blade (142) extends distally from cap (134). Clamp arm (144) is an integral feature of clamp arm assembly (150). Clamp arm (144) includes a clamp pad (146) facing ultrasonic blade (142). Clamp arm assembly (150) is pivotally coupled with outer sheath (132) via a pin (156). Clamp arm (144) is positioned distal to pin (156); while shank (152) and thumb grip ring (154) are positioned proximal to pin (156). Thus, as shown in FIGS. 3-4, clamp arm (144) is pivotable toward and away from ultrasonic blade (142) based on pivoting of thumb grip ring (154) toward and away from body (122) of handle assembly (120). It should therefore be understood that an operator may squeeze thumb grip ring (154) toward body (122) to thereby clamp tissue between clamp pad (146) and ultrasonic blade (142) to transect and/or seal the tissue. In some versions, one or more resilient members are used to bias clamp arm (144) to the open position shown in FIG. 3. By way of example only, such a resilient member may comprise a leaf spring, a torsion spring, and/or any other suitable kind of resilient member.

Referring back to FIG. 1, an ultrasonic transducer assembly (112) extends proximally from body (122) of handle assembly (120). Transducer assembly (112) is coupled with a generator (116) via a cable (114). Transducer assembly (112) receives electrical power from generator (116) and converts that power into ultrasonic vibrations through piezoelectric principles. Generator (116) may include a power source and control module that is configured to provide a power profile to transducer assembly (112) that is particularly suited for the generation of ultrasonic vibrations through transducer assembly (112). By way of example only, generator (116) may comprise a GEN 300 sold by Ethicon Endo-Surgery, Inc. of Cincinnati, Ohio. In addition or in the alternative, generator (116) may be constructed in accordance with at least some of the teachings of U.S. Pub. No. 2011/0087212, entitled "Surgical Generator for Ultrasonic and Electrosurgical Devices," published Apr. 14, 2011, the disclosure of which is incorporated by reference herein. It should also be understood that at least some of the functionality of generator (116) may be integrated into handle assembly (120), and that handle assembly (120) may even include a battery or other on-board power source such that cable (114) is omitted. Still other suitable forms that generator (116) may take, as well as various features and operabilities that generator (116) may provide, will be apparent to those of ordinary skill in the art in view of the teachings herein.

Ultrasonic vibrations that are generated by transducer assembly (112) are communicated along an acoustic waveguide (138), which extends through shaft assembly (130) to reach ultrasonic blade (142). Waveguide (138) is secured within shaft assembly (130) via a pin (not shown), which passes through waveguide (138) and shaft assembly (130). This pin is located at a position along the length of waveguide (138) corresponding to a node associated with resonant ultrasonic vibrations communicated through waveguide (138). As noted above, when ultrasonic blade (142) is in an activated state (i.e., vibrating ultrasonically), ultrasonic blade (142) is operable to effectively cut through and seal tissue, particularly when the tissue is being clamped between clamp pad (146) and ultrasonic blade (142). It should be understood that waveguide (138) may be configured to amplify mechanical vibrations transmitted through waveguide (138). Furthermore, waveguide (138) may include features operable to control the gain of the longitudinal vibrations along waveguide (138) and/or features to tune waveguide (138) to the resonant frequency of the system.

In the present example, the distal end of ultrasonic blade (142) is located at a position corresponding to an anti-node associated with resonant ultrasonic vibrations communicated through waveguide (138), in order to tune the acoustic assembly to a preferred resonant frequency $f_o$ when the acoustic assembly is not loaded by tissue. When transducer assembly (112) is energized, the distal end of ultrasonic blade (142) is configured to move longitudinally in the range of, for example, approximately 10 to 500 microns peak-to-peak, and in some instances in the range of about 20 to about 200 microns at a predetermined vibratory frequency $f_o$ of, for example, 55.5 kHz. When transducer assembly (112) of the present example is activated, these mechanical oscillations are transmitted through the waveguide to reach ultrasonic blade (102), thereby providing oscillation of ultrasonic blade (102) at the resonant ultrasonic frequency. Thus, when tissue is secured between ultrasonic blade (142) and clamp pad (46), the ultrasonic oscillation of ultrasonic blade (142) may simultaneously sever the tissue and denature the proteins in adjacent tissue cells, thereby providing a coagulative effect with relatively little thermal spread. In some versions, an electrical current may also be provided through ultrasonic blade (142) and/or clamp pad (146) to also seal the tissue.

An operator may activate buttons (126) to selectively activate transducer assembly (112) to thereby activate ultrasonic blade (142). In the present example, two buttons (126) are provided-one for activating ultrasonic blade (142) at a low power and another for activating ultrasonic blade (142) at a high power. However, it should be understood that any other suitable number of buttons and/or otherwise selectable power levels may be provided. For instance, a foot pedal may be provided to selectively activate transducer assembly (112). Buttons (126) of the present example are positioned such that an operator may readily fully operate instrument (100) with a single hand. For instance, the operator may position their thumb in thumb grip ring (154), position their ring finger in finger grip ring (124), position their middle finger about body (122), and manipulate buttons (126) using their index finger. Of course, any other suitable techniques may be used to grip and operate instrument (100); and buttons (126) may be located at any other suitable positions.

The foregoing components and operabilities of instrument (100) are merely illustrative. Instrument (100) may be configured in numerous other ways as will be apparent to those of ordinary skill in the art in view of the teachings herein. By way of example only, at least part of instrument (100) may be constructed and/or operable in accordance with at least some of the teachings of any of the following, the disclosures of which are all incorporated by reference herein: U.S. Pat. Nos. 5,322,055; 5,873,873; 5,980,510;

6,325,811; 6,783,524; U.S. Pub. No. 2006/0079874; U.S. Pub. No. 2007/0191713; U.S. Pub. No. 2007/0282333; U.S. Pub. No. 2008/0200940; U.S. Pub. No. 2010/0069940; U.S. Pub. No. 2011/0015660; U.S. Pub. No. 2012/0112687; U.S. Pub. No. 2012/0116265; U.S. Pub. No. 2014/0005701; U.S. Pub. No. 2014/0114334; and/or U.S. patent application Ser. No. 14/031,665. Additional merely illustrative variations for instrument (100) will be described in greater detail below. It should be understood that the below described variations may be readily applied to instrument (100) described above and any of the instruments referred to in any of the references that are cited herein, among others.

II. Surgical Instrument with Integral Hinge Coupling Features

In some instances, it may be desirable to pivotally couple clamp arm assembly (150) with outer sheath (132) without a separate pin (156), such as for simplifying the process of assembling instrument (100) and/or for reducing the quantity of individual components of instrument (100). In addition, or alternatively, it may be desirable to form outer sheath (132) from a non-metal material, such as a plastic material, in order to reduce manufacturing costs and/or reduce operating temperatures; and to do so without sacrificing the mechanical strength and/or dimensional accuracy of outer sheath (132), such as by avoiding warpage of outer sheath (132) during post-molding cooling, which might otherwise result in undesirable misalignment of ultrasonic blade (142). Each of the examples of instruments (3100, 3200, 3300, 3400, 3500, 3600) described below provides one or more of such functionalities. While the features set forth below are described in the context of ultrasonic surgical instruments (3100, 3200, 3300, 3400, 3500, 3600), it will be appreciated that such features may be readily incorporated into other suitable types of surgical instruments, such as electrosurgical (e.g., bipolar) instruments.

A. Instrument with Pair of Pivot Bosses on Shaft Assembly

FIGS. 5-8 show another example of an ultrasonic surgical instrument (3100) that is operable to cut tissue and seal or weld tissue (e.g., a blood vessel, etc.) substantially simultaneously. Instrument (3100) may be similar to instrument (100) described above, except as otherwise described below. In this regard, instrument (3100) of this example comprises a handle assembly (3120), a shaft assembly (3130), and an end effector (3140). Handle assembly (3120) comprises a body (3122) including a finger grip ring (3124) and a pair of buttons (3126). Instrument (3100) also includes a clamp arm assembly (3150) that is pivotable toward and away from body (3122). Clamp arm assembly (3150) includes a shank (3152) with a thumb grip ring (3154). A pair of side members (3153) of clamp arm assembly (3150) are disposed about a distal portion of shaft assembly (3130). Shaft assembly (3130) comprises an outer sheath (also referred to as a "pivot shaft") (3132) extending distally from body (3122). A cap (3134) is secured to the distal end of sheath (3132). End effector (3140) comprises an ultrasonic blade (3142) and a clamp arm (3144). Ultrasonic blade (3142) extends distally from cap (3134). Clamp arm (3144) is an integral feature of clamp arm assembly (3150). Clamp arm (3144) includes a clamp pad (3146) facing ultrasonic blade (3142).

In the example shown, clamp arm assembly (3150) is pivotally coupled with outer sheath (3132). In this regard, outer sheath (3132) of the present example includes an upwardly-extending projection (also referred to as a "fin") (3155) and a laterally-opposed pair of first pivot members in the form of generally cylindrical bosses (3156) extending laterally outwardly from opposing sides of fin (3155); while clamp arm assembly (3150) of the present example includes a laterally-opposed pair of second pivot members in the form of generally C-shaped receptacles (3158) provided on laterally inner sides of corresponding side members (3153) that are each configured to securely and pivotally retain a corresponding boss (3156). For example, each receptacle (3158) may be configured to provide a snap-fit engagement with the corresponding boss (3156), with such a snap-fit engagement permitting rotation of bosses (3156) relative to receptacles (3158) about a pivot axis collectively defined by bosses (3156) and receptacles (3158). In the example shown, clamp arm assembly (3150) also includes a laterally-opposed pair of generally circular bores (3159) extending laterally through corresponding side members (3153) and aligned with corresponding receptacles (3158). In some versions, bosses (3156) may be configured to flex laterally inwardly toward each other to facilitate insertion of bosses (3156) between side members (3153) when bosses (3156) are being directed toward receptacles (3158), and to resiliently extend laterally outwardly into corresponding bores (3159) when aligned therewith. Clamp arm (3144) is positioned distal to bosses (3156) and receptacles (3158); while shank (3152) and thumb grip ring (3154) are positioned proximal to bosses (3156) and receptacles (3158). Thus, clamp arm (3144) is pivotable toward and away from ultrasonic blade (3142) based on pivoting of thumb grip ring (3154) toward and away from body (3122) of handle assembly (3120) in a manner similar to that described above. It should therefore be understood that an operator may squeeze thumb grip ring (3154) toward body (3122) to thereby clamp tissue between clamp pad (3146) and ultrasonic blade (3142) to transect and/or seal the tissue. In some versions, one or more resilient members are used to bias clamp arm (3144) to the open position.

Bosses (3156) of the present example are integrally formed together with fin (3155) and the rest of outer sheath (3132) as a unitary (e.g., monolithic) piece. For example, bosses (3156) may be integrally formed together with fin (3155) and the rest of outer sheath (3132) via a molding (e.g., injection molding) process. Thus, bosses (3156) and receptacles (3158) may enable pivotal coupling of clamp arm assembly (3150) with outer sheath (3132) without requiring a separate pin, such as pin (156). In some versions, outer sheath (3132), including bosses (3156), may be formed of a plastic material. In addition, or alternatively, bosses (3156) may be formed of a material different from that of receptacles (3158), such as to facilitate smooth relative motion between bosses (3156) and receptacles (3158) during pivoting of clamp arm (3144) relative to ultrasonic blade (3142). For example, receptacles (3158) may be formed of a non-plastic material, such as a metal material, in some versions in which bosses (3156) are formed of a plastic material. As another example, receptacles (3158) may be formed of a plastic material that is different from that of bosses (3156).

An ultrasonic transducer assembly (not shown) similar to ultrasonic transducer assembly (112) may extend proximally from body (3122) of handle assembly (3120). The transducer assembly may be coupled with a generator (not shown), such as generator (116), via a cable (not shown), such as cable (114). The transducer assembly may receive electrical power from the generator and convert that power into ultrasonic vibrations through piezoelectric principles. Ultrasonic vibrations that are generated by the transducer assembly may be communicated along an acoustic waveguide (3138), which extends through shaft assembly (3130) to reach ultrasonic blade (3142). Waveguide (3138) is secured within shaft assembly (3130) via a pin (not shown), which passes through waveguide (3138) and shaft assembly (3130). When tissue is secured between ultrasonic blade (3142) and clamp pad (3146), the ultrasonic oscillation of ultrasonic blade (3142) may simultaneously sever the tissue and denature the proteins in adjacent tissue cells, thereby providing a coagulative effect with relatively little thermal spread in a manner similar to that described above. In some versions, an electrical current may also be provided through ultrasonic blade (3142) and/or clamp pad (3146) to also seal the tissue. An operator may activate buttons (3126) to selectively activate the transducer assembly to thereby activate ultrasonic blade (3142). In the present example, two buttons (3126) are provided-one for activating ultrasonic blade (3142) at a low power and another for activating ultrasonic blade (3142) at a high power. However, it should be understood that any other suitable number of buttons and/or otherwise selectable power levels may be provided.

In addition to the foregoing, instrument (3110) may be configured and operable in accordance with at least some of the teachings of U.S. Pat. No. 11,051,835, entitled "Alignment Features for Ultrasonic Surgical Instrument," issued Jul. 6, 2021, the disclosure of which is incorporated by reference herein.

B. Instrument with Single Pivot Boss on Clamp Arm Assembly

Figure 9:
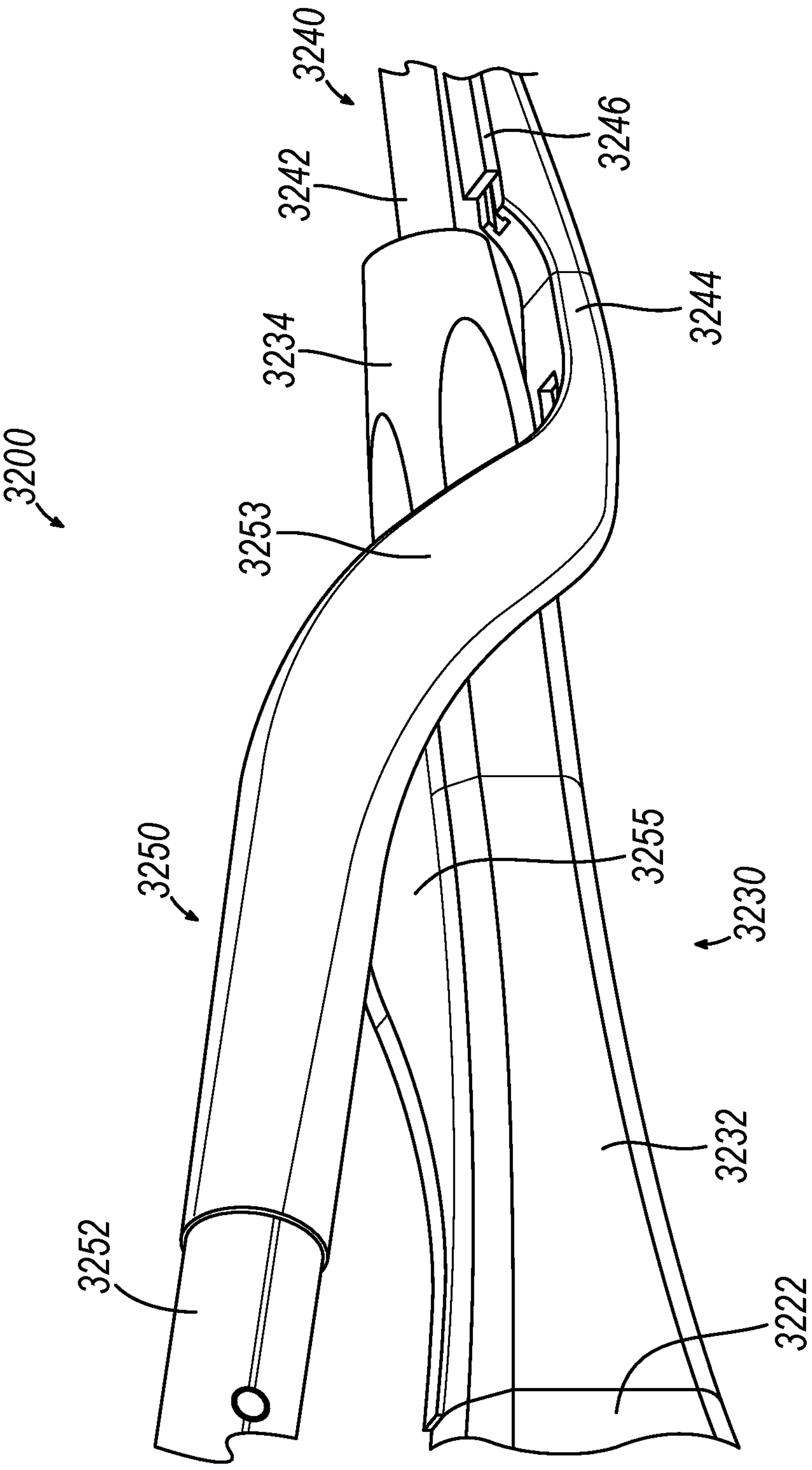
FIG. 9 depicts an enlarged perspective view of another example of a surgical instrument including a clamp arm assembly pivotally coupled to a shaft assembly, and having a single pivot boss on the clamp arm assembly that is received within a receptacle on the shaft assembly.
Figure 10:
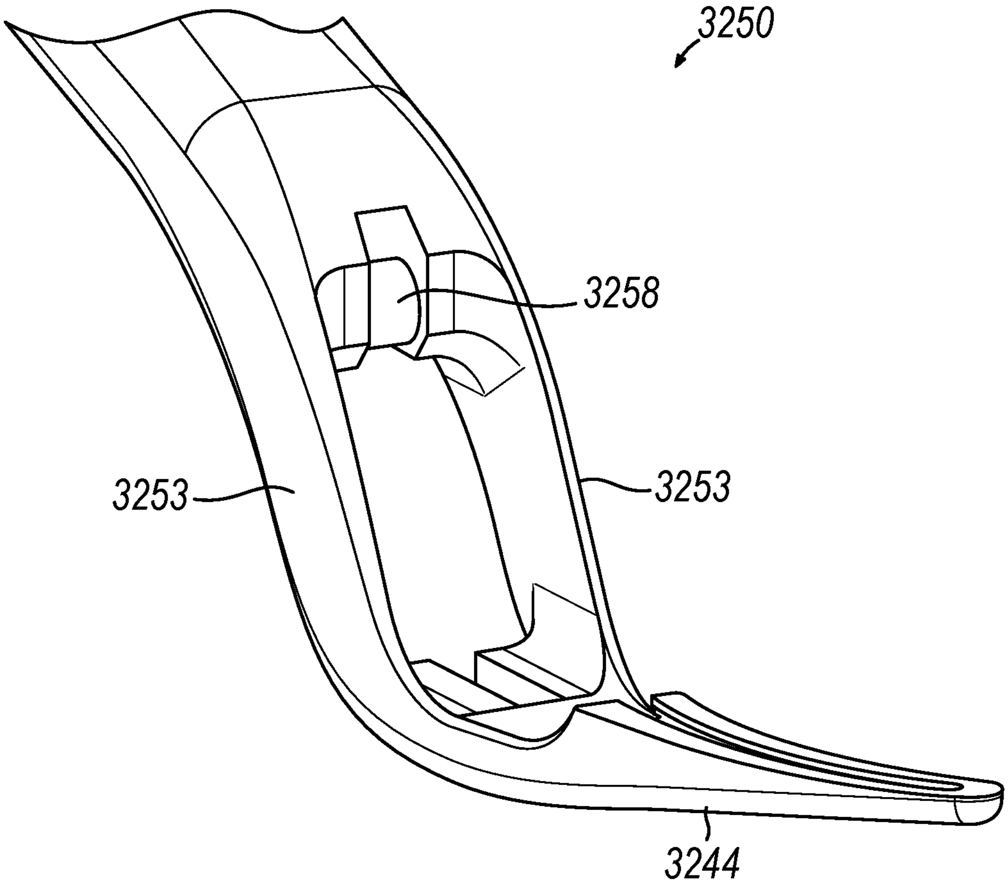
FIG. 10 depicts an enlarged perspective view of the clamp arm assembly of FIG. 9.
Figure 11:
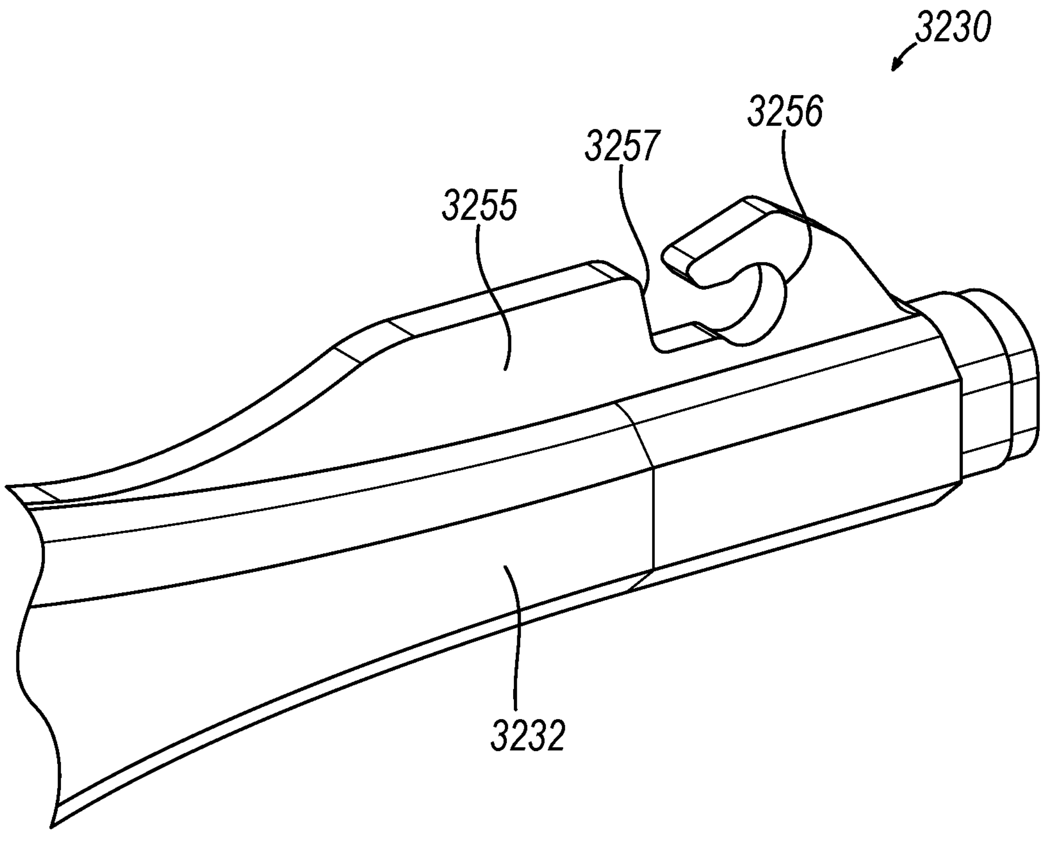
FIG. 11 depicts an enlarged perspective view of the shaft assembly of FIG. 9.

FIGS. 9-11 show another example of an ultrasonic surgical instrument (3200) that is operable to cut tissue and seal or weld tissue (e.g., a blood vessel, etc.) substantially simultaneously. Instrument (3200) may be similar to instrument (3100) described above, except as otherwise described below. In this regard, instrument (3200) of this example comprises a handle assembly (not shown) similar to handle assembly (3120), a shaft assembly (3230), and an end effector (3240). The handle assembly comprises a body (3222). Instrument (3200) also includes a clamp arm assembly (3250) that is pivotable toward and away from body (3222). Clamp arm assembly (3250) includes a shank (3252) with a thumb grip ring (not shown) similar to thumb grip ring (3154). A pair of side members (3253) of clamp arm assembly (3250) are disposed about a distal portion of shaft assembly (3230). Shaft assembly (3230) comprises an outer sheath (also referred to as a "pivot shaft") (3232) extending distally from body (3222). A cap (3234) is secured to the distal end of sheath (3232). End effector (3240) comprises an ultrasonic blade (3242) and a clamp arm (3244). Ultrasonic blade (3242) extends distally from cap (3234). Clamp arm (3244) is an integral feature of clamp arm assembly (3250). Clamp arm (3244) includes a clamp pad (3246) facing ultrasonic blade (3242).

In the example shown, clamp arm assembly (3250) is pivotally coupled with outer sheath (3232). In this regard, outer sheath (3232) of the present example includes an upwardly-extending projection (also referred to as a "fin") (3255) and a first pivot member in the form of a generally C-shaped receptacle (3256) that extends laterally through fin (3255) and that is open to an upper edge of fin (3255) via a generally L-shaped slot (3257); while clamp arm assembly (3250) of the present example includes a second pivot member in the form of a generally cylindrical boss (3258) extending laterally between side members (3253) that is configured to be securely and pivotally retained by receptacle (3256) and that is configured to be inserted into receptacle (3256) via slot (3257). For example, receptacle (3256) may be configured to provide a snap-fit engagement with boss (3258), with such a snap-fit engagement permitting rotation of boss (3258) relative to receptacle (3256) about a pivot axis collectively defined by boss (3258) and receptacle (3256). Clamp arm (3244) is positioned distal to boss (3258) and receptacle (3256); while shank (3252) and the thumb grip ring are positioned proximal to receptacle (3256) and boss (3258). Thus, clamp arm (3244) is pivotable toward and away from ultrasonic blade (3242) based on pivoting of the thumb grip ring toward and away from body (3222) of the handle assembly in a manner similar to that described above. It should therefore be understood that an operator may squeeze the thumb grip ring toward body (3222) to thereby clamp tissue between clamp pad (3246) and ultrasonic blade (3242) to transect and/or seal the tissue. In some versions, one or more resilient members are used to bias clamp arm (3244) to the open position.

Boss (3258) of the present example is integrally formed together with clamp arm (3244) as a unitary (e.g., monolithic) piece. For example, boss (3258) may be integrally formed together with clamp arm (3244) via a molding (e.g., injection molding) process. Thus, boss (3258) and receptacle (3256) may enable pivotal coupling of clamp arm assembly (3250) with outer sheath (3232) without requiring a separate pin, such as pin (156). In some versions, boss (3258) may be formed of a plastic material. In addition, or alternatively, boss (3258) may be formed of a material different from that of receptacle (3256), such as to facilitate smooth relative motion between boss (3258) and receptacle (3256) during pivoting of clamp arm (3244) relative to ultrasonic blade (3242). For example, receptacle (3256) may be formed of a plastic material that is different from that of boss (3258).

C. Instrument with Pair of Pivot Bosses on Clamp Arm Assembly

Figure 12:
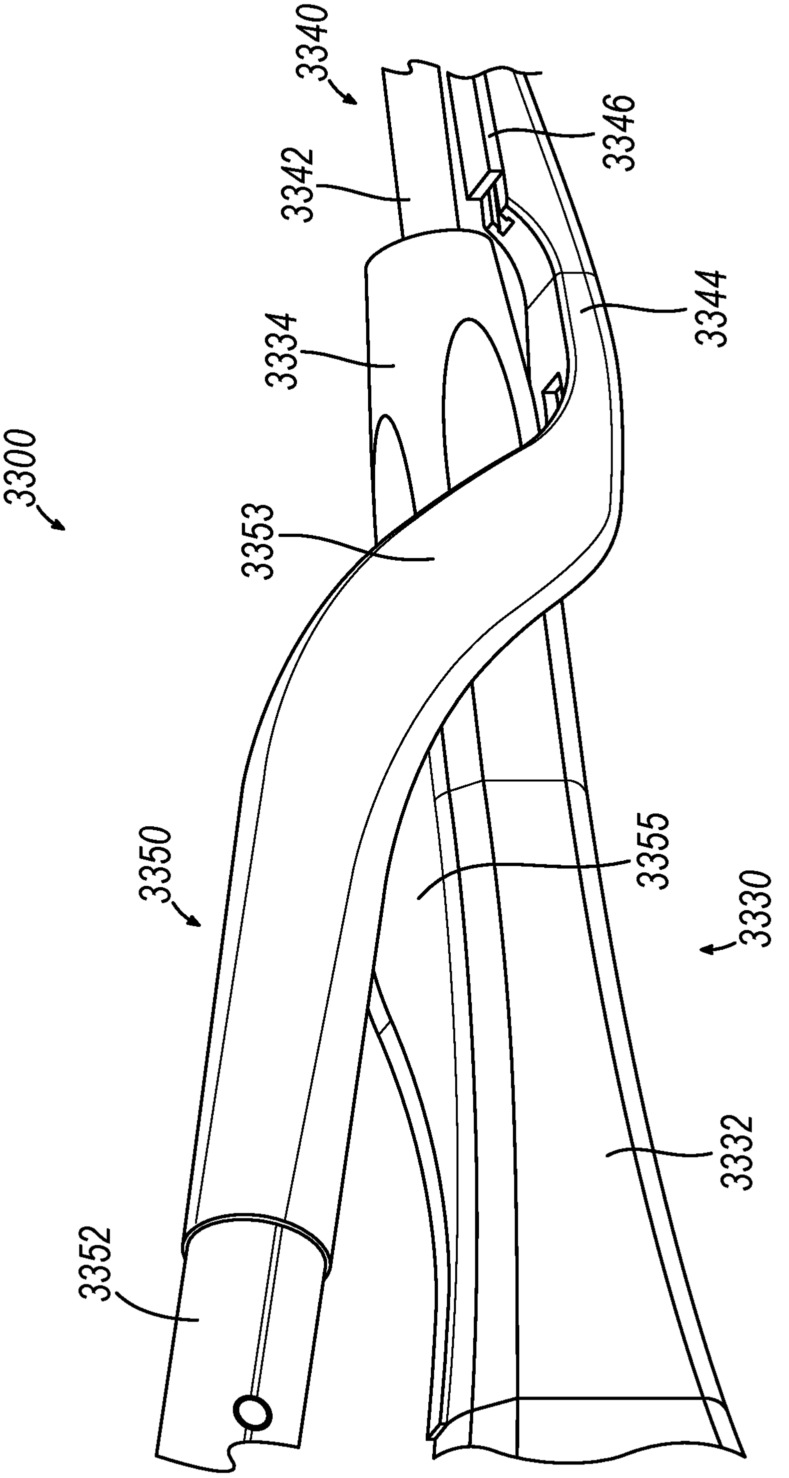
FIG. 12 depicts an enlarged perspective view of another example of a surgical instrument including a clamp arm assembly pivotally coupled to a shaft assembly, and having a pair of pivot bosses on the clamp arm assembly that are received within corresponding receptacles on the shaft assembly.
Figure 13:
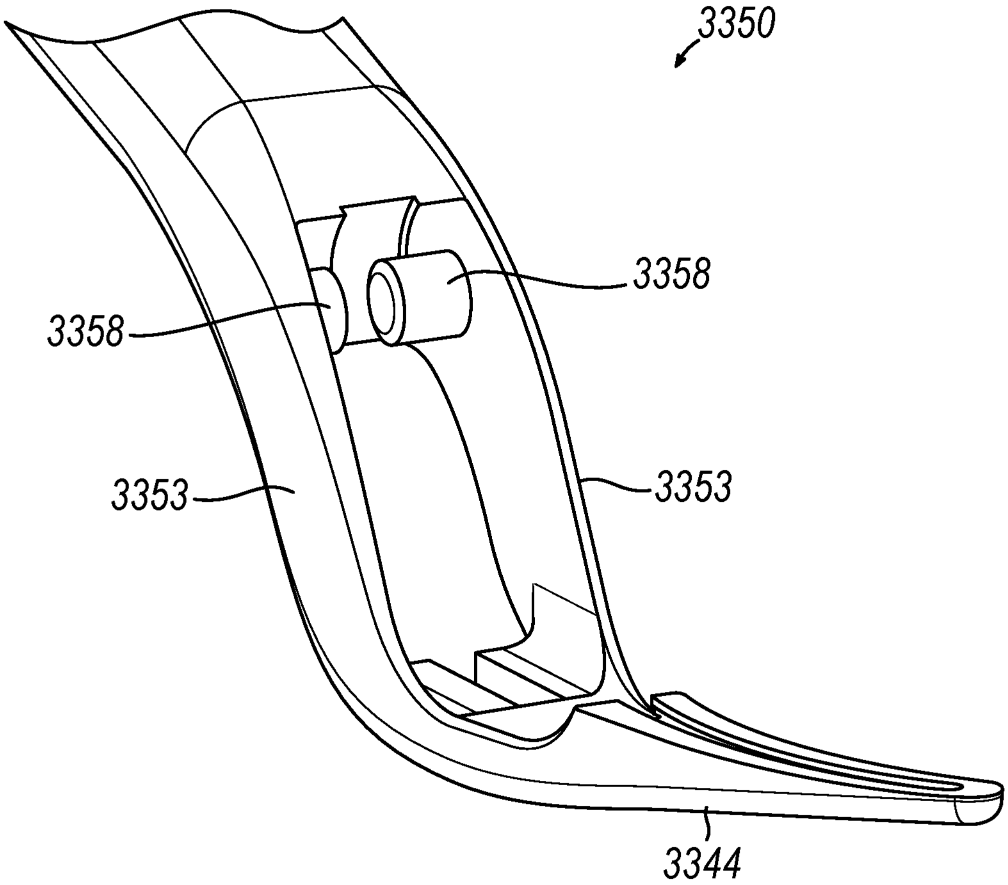
FIG. 13 depicts an enlarged perspective view of the clamp arm assembly of FIG. 12.
Figure 14:
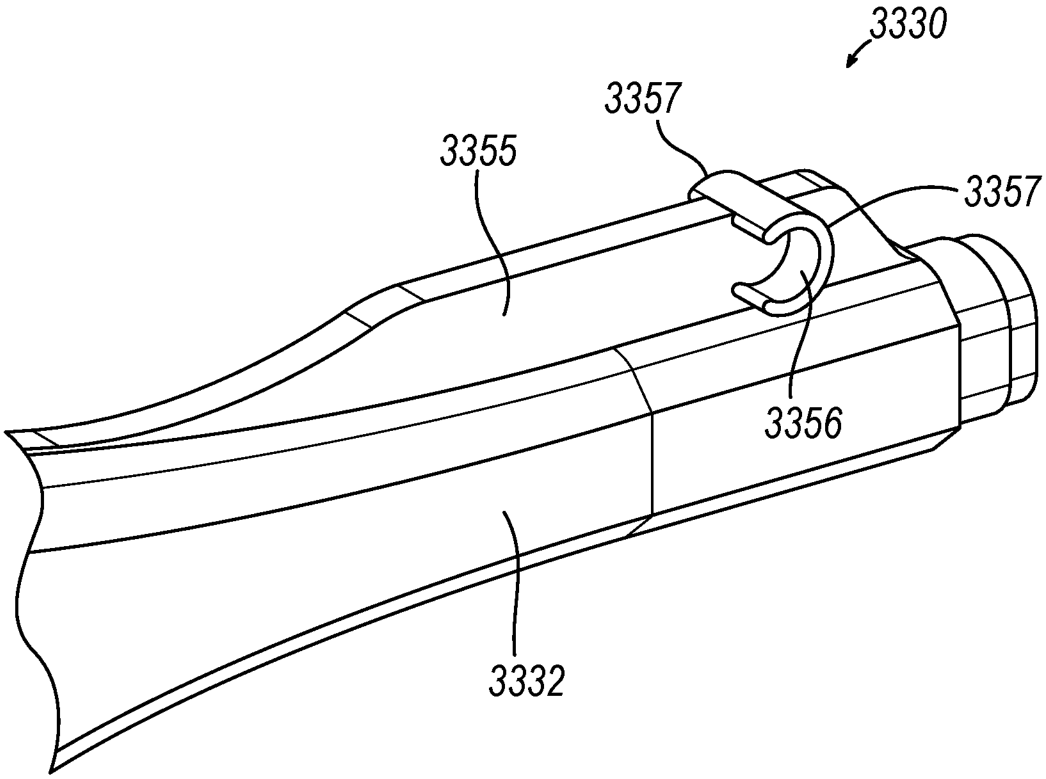
FIG. 14 depicts an enlarged perspective view of the shaft assembly of FIG. 12.
Figure 15:
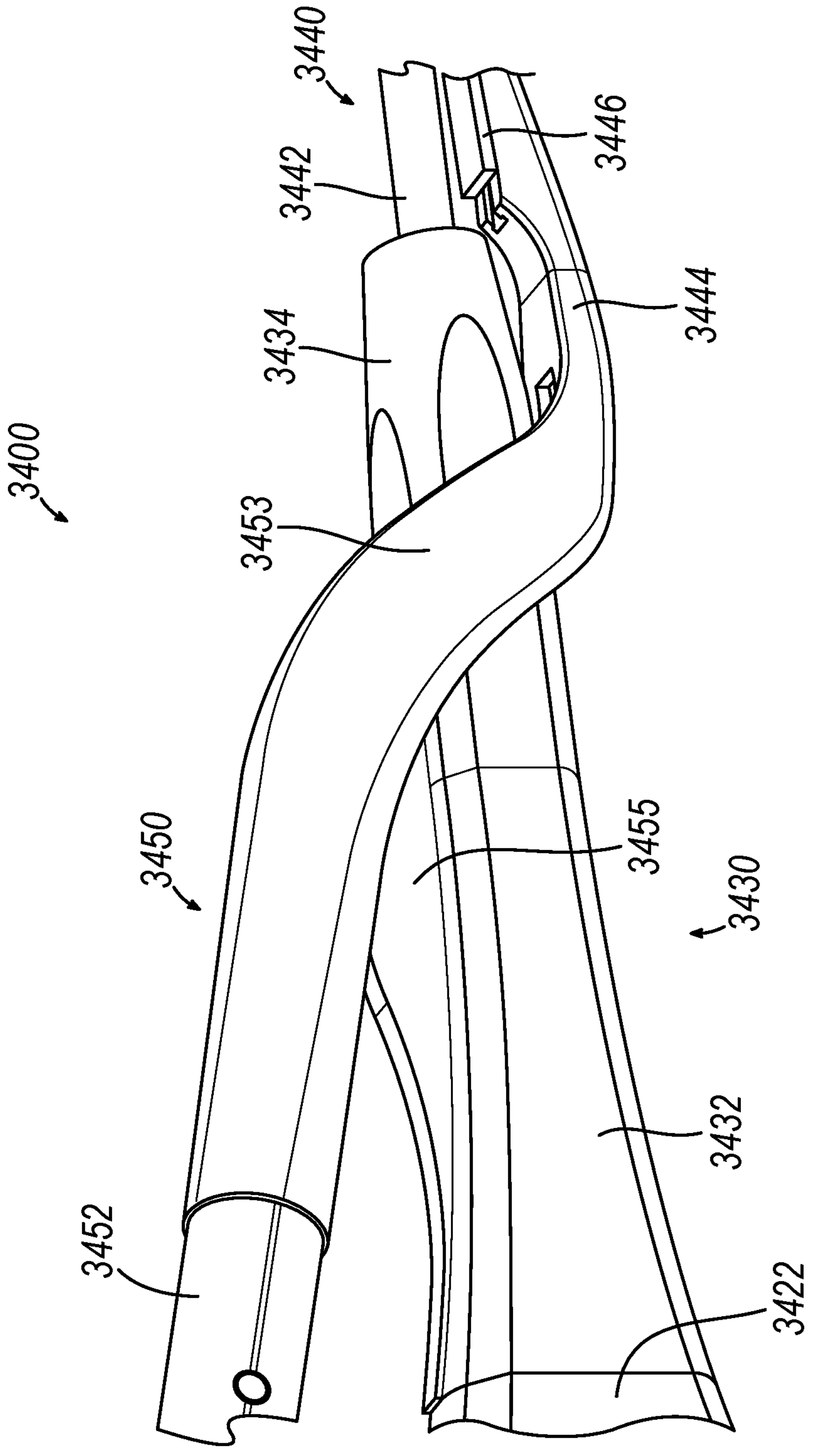
FIG. 15 depicts an enlarged perspective view of another example of a surgical instrument including a clamp arm assembly pivotally coupled to a shaft assembly, and having a pair of flexible pivot bosses on the clamp arm assembly that are received within a receptacle on the shaft assembly.
Figure 16:
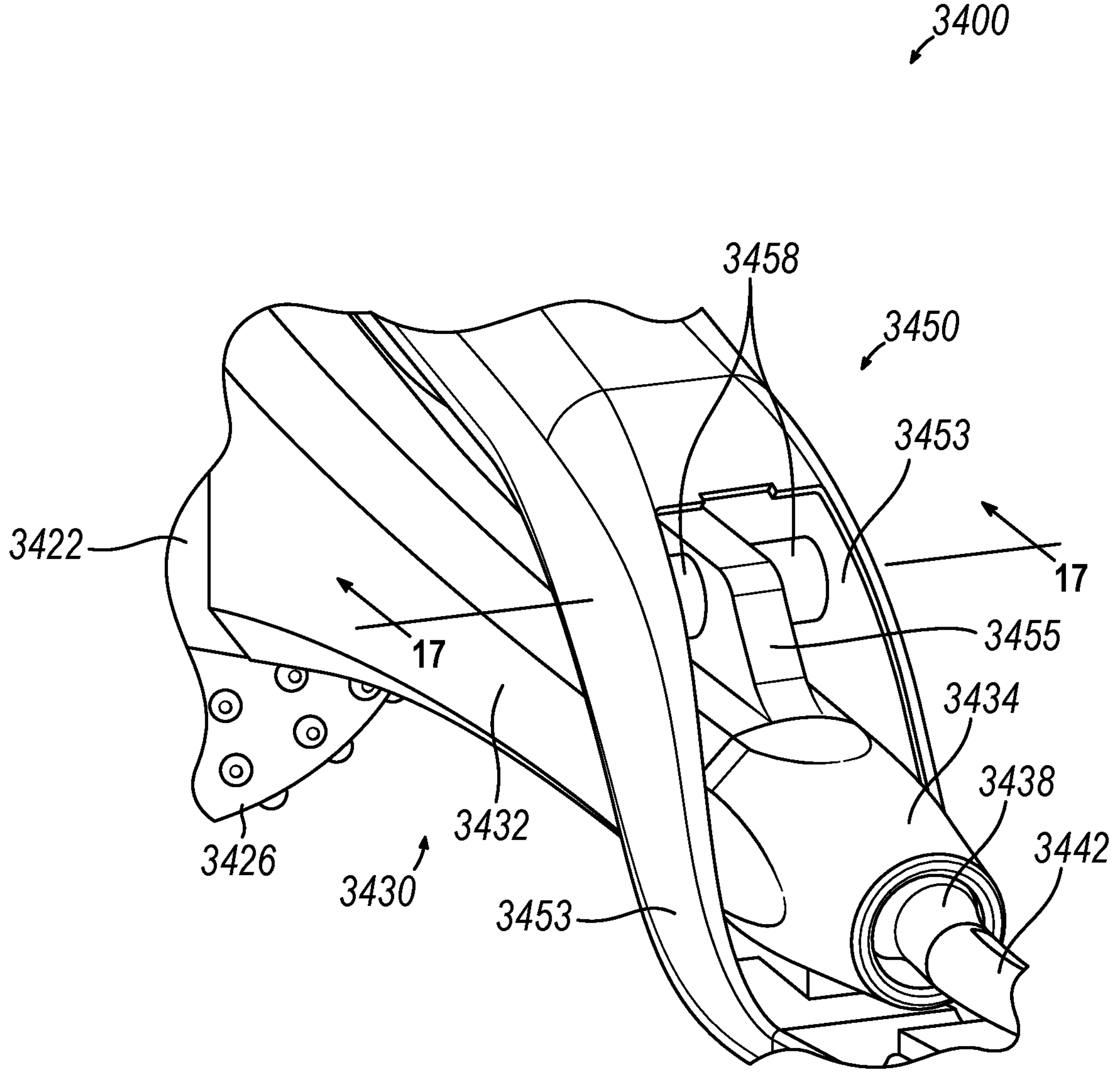
FIG. 16 depicts an enlarged perspective view of the surgical instrument of FIG. 15.
Figure 17:
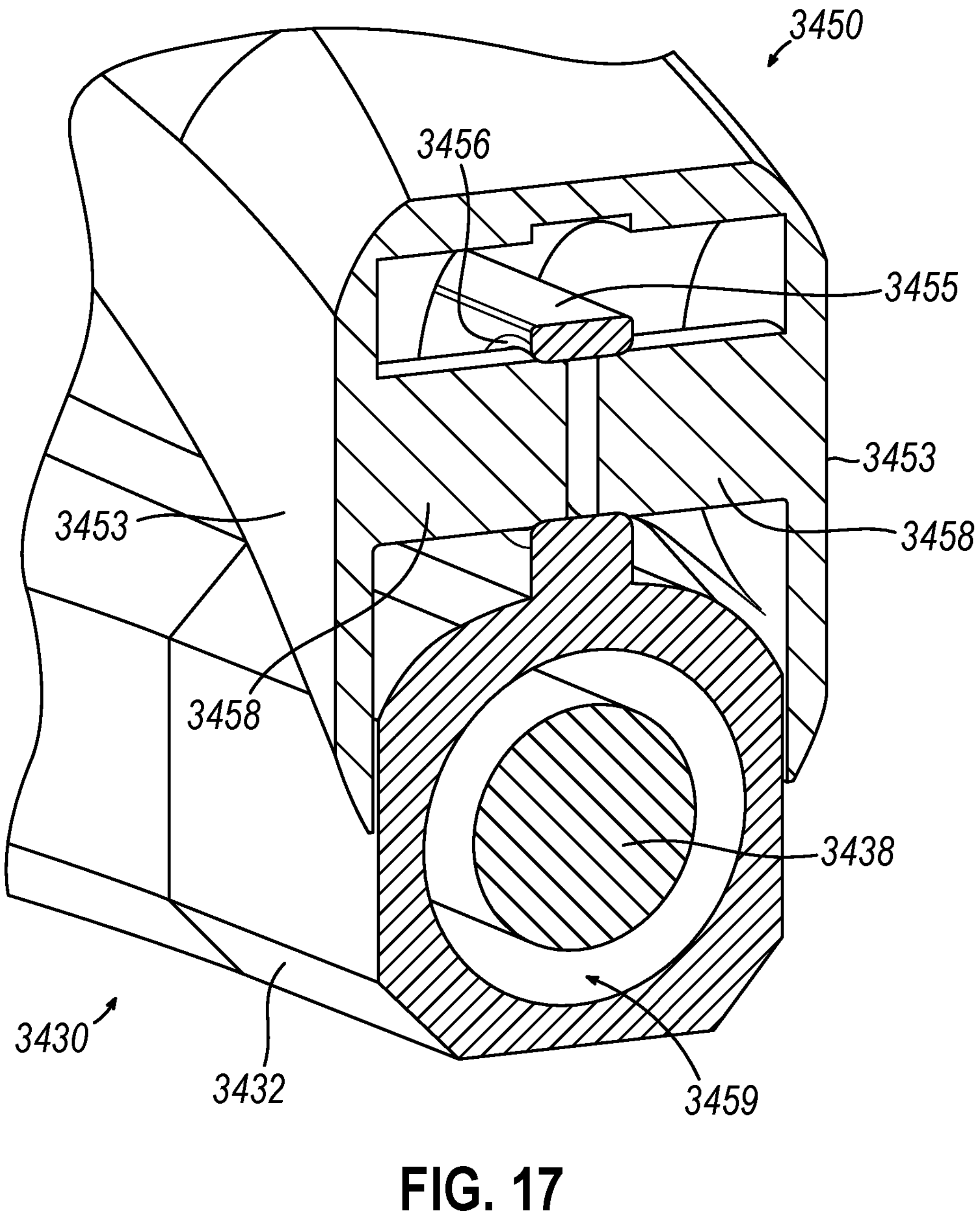
FIG. 17 depicts an enlarged perspective sectional view of the surgical instrument of FIG. 15, taken along section line 17-17 of FIG. 16.
Figure 18:
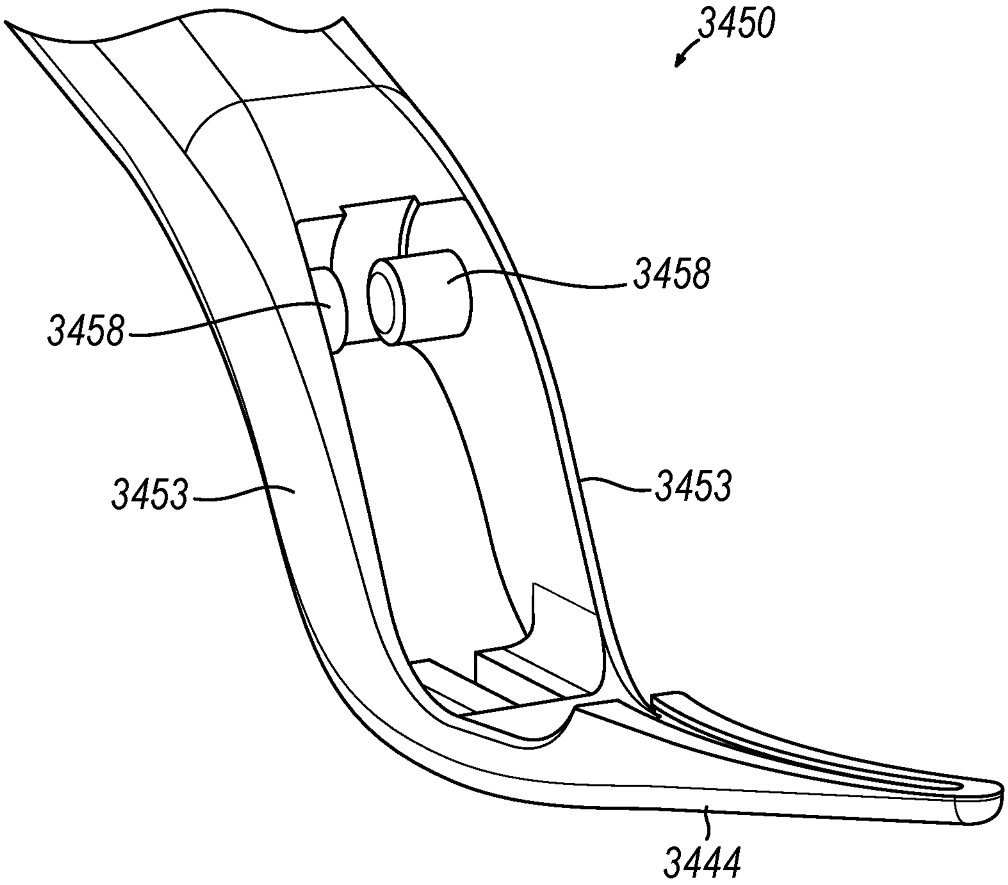
FIG. 18 depicts an enlarged perspective view of the clamp arm assembly of FIG. 15.
Figure 19:
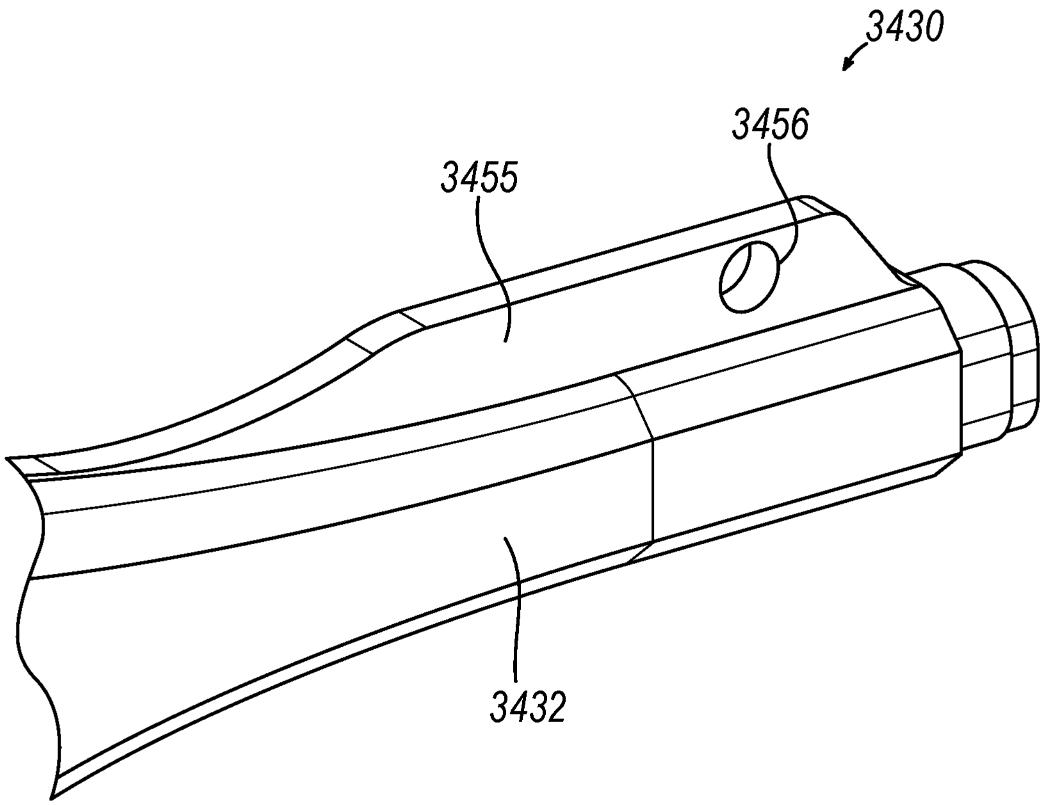
FIG. 19 depicts an enlarged perspective view of the shaft assembly of FIG. 15.

FIGS. 12-14 show another example of an ultrasonic surgical instrument (3300) that is operable to cut tissue and seal or weld tissue (e.g., a blood vessel, etc.) substantially simultaneously. Instrument (3300) may be similar to instrument (3100) described above, except as otherwise described below. In this regard, instrument (3300) of this example comprises a handle assembly (not shown) similar to handle assembly (3120), a shaft assembly (3330), and an end effector (3340). Instrument (3300) also includes a clamp arm assembly (3350) that is pivotable toward and away from the body of the handle assembly. Clamp arm assembly (3350) includes a shank (3352) with a thumb grip ring (not shown) similar to thumb grip ring (3154). A pair of side members (3353) of clamp arm assembly (3350) are disposed about a distal portion of shaft assembly (3330). Shaft assembly (3330) comprises an outer sheath (also referred to as a "pivot shaft") (3332) extending distally from the body of the handle assembly. A cap (3334) is secured to the distal end of sheath (3332). End effector (3340) comprises an ultrasonic blade (3342) and a clamp arm (3344). Ultrasonic blade (3342) extends distally from cap (3334). Clamp arm (3344) is an integral feature of clamp arm assembly (3350). Clamp arm (3344) includes a clamp pad (3346) facing ultrasonic blade (3342).

In the example shown, clamp arm assembly (3350) is pivotally coupled with outer sheath (3332). In this regard, outer sheath (3332) of the present example includes an upwardly-extending projection (also referred to as a "fin") (3355) and a laterally-opposed pair of first pivot members in the form of generally C-shaped receptacles (3356) defined by corresponding generally C-shaped flanges (3357) extending laterally outwardly from opposing sides of fin (3355); while clamp arm assembly (3350) of the present example includes a laterally-opposed pair of second pivot members in the form of generally cylindrical bosses (3358) extending laterally inwardly from laterally inner sides of corresponding side members (3353) that are each configured to be securely and pivotally retained by a corresponding receptacle (3356). For example, each receptacle (3356) may be configured to provide a snap-fit engagement with the corresponding boss (3358), with such a snap-fit engagement permitting rotation of bosses (3358) relative to receptacles (3356) about a pivot axis collectively defined by bosses (3358) and receptacles (3356). Clamp arm (3344) is positioned distal to bosses (3358) and receptacles (3356); while shank (3352) and the thumb grip ring are positioned proximal to receptacles (3356) and bosses (3358). Thus, clamp arm (3344) is pivotable toward and away from ultrasonic blade (3342) based on pivoting of the thumb grip ring toward and away from the body of the handle assembly in a manner similar to that described above. It should therefore be understood that an operator may squeeze the thumb grip ring toward the body of the handle assembly to thereby clamp tissue between clamp pad (3346) and ultrasonic blade (3342) to transect and/or seal the tissue. In some versions, one or more resilient members are used to bias clamp arm (3344) to the open position.

Bosses (3358) of the present example are integrally formed together with clamp arm (3344) as a unitary (e.g., monolithic) piece. For example, bosses (3358) may be integrally formed together with clamp arm (3344) via a molding (e.g., injection molding) process. Similarly, flanges (3357) of the present example are integrally formed together with fin (3355) and the rest of outer sheath (3332) as a unitary (e.g., monolithic) piece. For example, flanges (3357) may be integrally formed together with fin (3355) and the rest of outer sheath (3332) via a molding (e.g., injection molding) process. Thus, bosses (3358) and receptacles (3356) may enable pivotal coupling of clamp arm assembly (3350) with outer sheath (3332) without requiring a separate pin, such as pin (156). In some versions, bosses (3358) may be formed of a plastic material. In addition, or alternatively, bosses (3358) may be formed of a material different from that of receptacles (3356), such as to facilitate smooth relative motion between bosses (3358) and receptacles (3356) during pivoting of clamp arm (3344) relative to ultrasonic blade (3342). For example, receptacles (3356) may be formed of a plastic material that is different from that of bosses (3358).

D. Instrument with Flexible Pivot Bosses on Clamp Arm Assembly

FIGS. 15-19 show another example of an ultrasonic surgical instrument (3400) that is operable to cut tissue and seal or weld tissue (e.g., a blood vessel, etc.) substantially simultaneously. Instrument (3400) may be similar to instrument (3100) described above, except as otherwise described below. In this regard, instrument (3400) of this example comprises a handle assembly (not shown) similar to handle assembly (3120), a shaft assembly (3430), and an end effector (3440). The handle assembly comprises a body (3422) and a pair of buttons (3426). Instrument (3400) also includes a clamp arm assembly (3450) that is pivotable toward and away from body (3422). Clamp arm assembly (3450) includes a shank (3452) with a thumb grip ring (not shown) similar to thumb grip ring (3154). A pair of side members (3453) of clamp arm assembly (3450) are disposed about a distal portion of shaft assembly (3430). Shaft assembly (3430) comprises an outer sheath (also referred to as a "pivot shaft") (3432) extending distally from body (3422). A cap (3434) is secured to the distal end of sheath (3432). End effector (3440) comprises an ultrasonic blade (3442) and a clamp arm (3444). Ultrasonic blade (3442) extends distally from cap (3434). Waveguide (3438) is secured within shaft assembly (3430) via a pin (not shown), which passes through waveguide (3438) and shaft assembly (3430). In this regard, outer sheath (3432) of the present example also includes a lumen (3459) configured to receive at least a portion of waveguide (3438). Clamp arm (3444) is an integral feature of clamp arm assembly (3450). Clamp arm (3444) includes a clamp pad (3446) facing ultrasonic blade (3442).

In the example shown, clamp arm assembly (3450) is pivotally coupled with outer sheath (3432). In this regard, outer sheath (3432) of the present example includes an upwardly-extending projection (also referred to as a "fin") (3455) and a first pivot member in the form of a generally circular receptacle (3456) that extends laterally through fin (3455); while clamp arm assembly (3450) of the present example includes a laterally-opposed pair of second pivot members in the form of generally cylindrical bosses (3458) extending laterally inwardly from laterally inner sides of corresponding side members (3453) that are each configured to be securely and pivotally retained by receptacle (3456). For example, receptacle (3456) may be configured to provide a snap-fit engagement with both bosses (3458), with such a snap-fit engagement permitting rotation of bosses (3458) relative to receptacle (3456) about a pivot axis collectively defined by bosses (3458) and receptacle (3456). In some versions, side members (3453) may be configured to flex laterally outwardly away from each other to facilitate insertion of fin (3455) between bosses (3458) when bosses (3458) are being directed toward receptacle (3456), and to resiliently extend laterally inwardly into receptacle (3456) when aligned therewith. Clamp arm (3444) is positioned distal to bosses (3458) and receptacle (3456); while shank (3452) and the thumb grip ring are positioned proximal to receptacle (3456) and bosses (3458). Thus, clamp arm (3444) is pivotable toward and away from ultrasonic blade (3442) based on pivoting of the thumb grip ring toward and away from body (3422) of the handle assembly in a manner similar to that described above. It should therefore be understood that an operator may squeeze the thumb grip ring toward body (3422) to thereby clamp tissue between clamp pad (3446) and ultrasonic blade (3442) to transect and/or seal the tissue. In some versions, one or more resilient members are used to bias clamp arm (3444) to the open position.

Bosses (3458) of the present example are integrally formed together with clamp arm (3444) as a unitary (e.g., monolithic) piece. For example, bosses (3458) may be integrally formed together with clamp arm (3444) via a molding (e.g., injection molding) process. Thus, bosses (3458) and receptacle (3456) may enable pivotal coupling of clamp arm assembly (3450) with outer sheath (3432) without requiring a separate pin, such as pin (156). In some versions, bosses (3458) may be formed of a plastic material. In addition, or alternatively, bosses (3458) may be formed of a material different from that of receptacle (3456), such as to facilitate smooth relative motion between bosses (3458) and receptacle (3456) during pivoting of clamp arm (3444) relative to ultrasonic blade (3442). For example, receptacle (3456) may be formed of a plastic material that is different from that of bosses (3458).

E. Shaft Assembly with Plastic Outer Sheath and Metal Insert Plate

Figure 20:
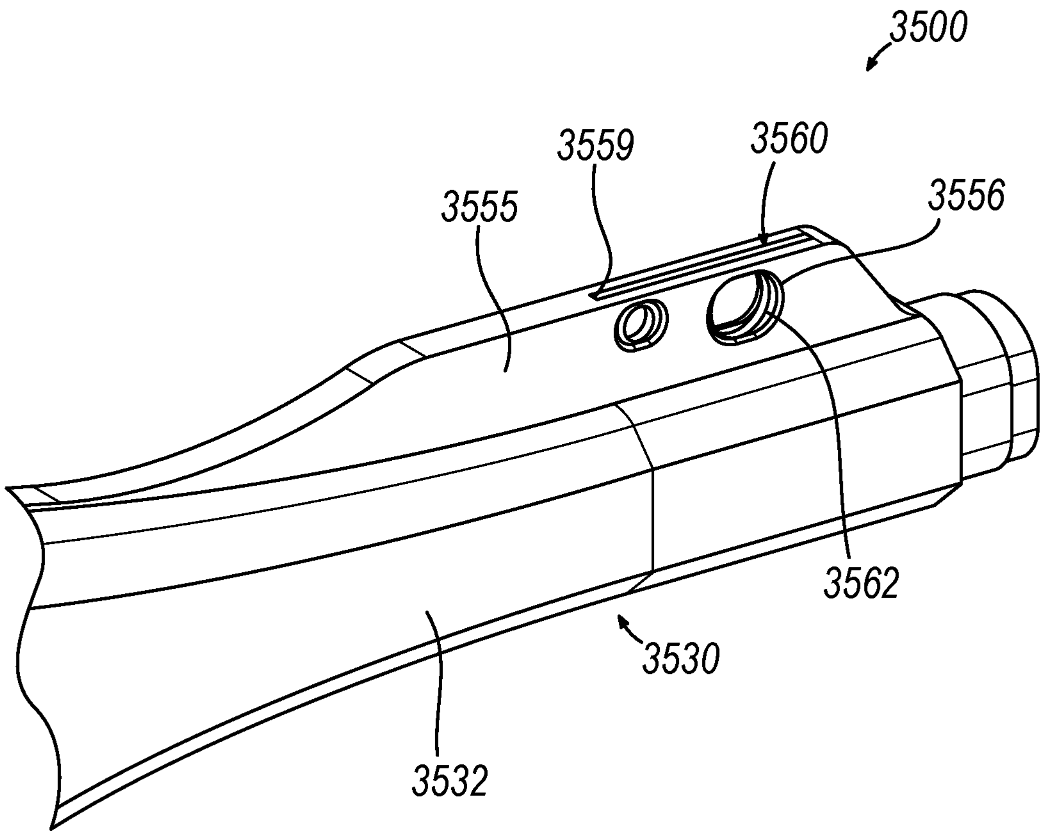
FIG. 20 depicts an enlarged perspective view of another example of a surgical instrument including a clamp arm assembly pivotally coupled to a shaft assembly, and having a metal insert plate disposed within a fin of the shaft assembly.
Figure 21:
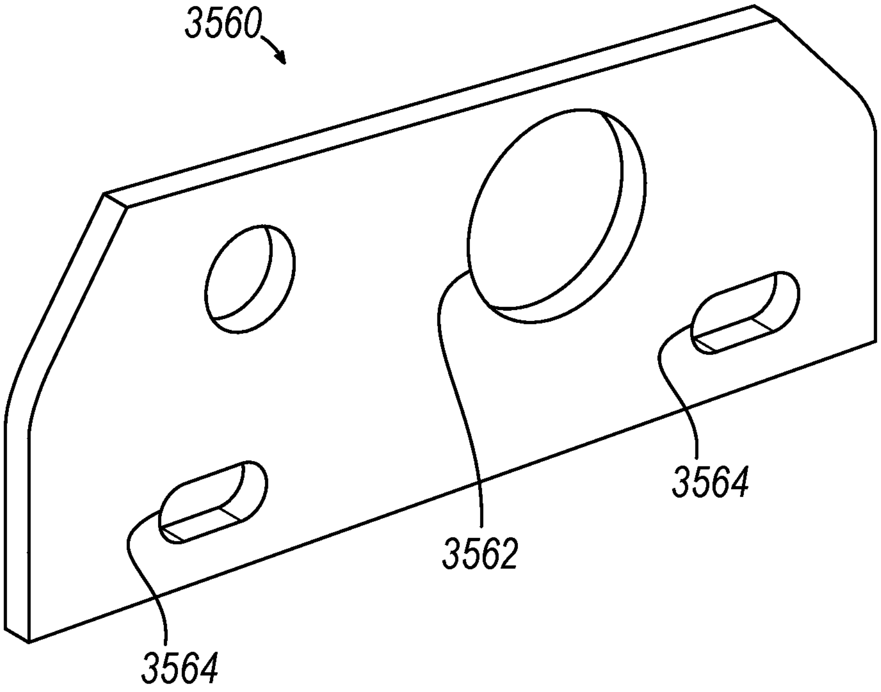
FIG. 21 depicts an enlarged perspective view of the metal insert plate of FIG. 20.

FIGS. 20-21 show another example of an ultrasonic surgical instrument (3500) that is operable to cut tissue and seal or weld tissue (e.g., a blood vessel, etc.) substantially simultaneously. Instrument (3500) may be similar to instrument (3400) described above, except as otherwise described below. In this regard, instrument (3500) of this example comprises a handle assembly (not shown) similar to handle assembly (3120), a shaft assembly (3530), and an end effector (not shown) similar to end effector (3440). Instrument (3500) also includes a clamp arm assembly (not shown) similar to clamp arm assembly (3450) that is pivotable toward and away from a body of the handle assembly. Shaft assembly (3530) comprises an outer sheath (also referred to as a "pivot shaft") (3532) extending distally from the body of the handle assembly. A cap (not shown) similar to cap (3434) is secured to the distal end of sheath (3532).

In the example shown, outer sheath (3532) is formed of a plastic material and is configured to be pivotally coupled with the clamp arm assembly. In this regard, outer sheath (3532) of the present example includes an upwardly-extending projection (also referred to as a "fin") (3555) and at least one first pivot member in the form of a generally circular receptacle (3556) that extends laterally through fin (3555) and that is configured to securely and pivotally retain at least one second pivot member (e.g., a pair of bosses) of the clamp arm assembly, such as in a manner similar to that described above. For example, the at least one receptacle (3556) may be configured to provide a snap-fit engagement with both bosses, with such a snap-fit engagement permitting rotation of both bosses relative to the at least one receptacle (3556) about a pivot axis collectively defined by the bosses and the at least one receptacle (3556). Outer sheath (3532) of the present example also includes a cavity (3559) disposed within fin (3555) that is open to an upper edge of fin (3555) and that intersects the at least one receptacle (3556).

In the example shown, shaft assembly (3530) further comprises a metal insert plate (3560) received within cavity (3559) of outer sheath (3532) and having a bore (3562) configured to be axially aligned with the at least one receptacle (3556), such that bore (3562) may securely and pivotally retain the at least one pivot member of the clamp arm assembly. Metal insert plate (3560) may be formed of sheet metal via a stamping process, for example. In addition, or alternatively, outer sheath (3532) may be overmolded onto metal insert plate (3560) via an injection molding process. In this regard, metal insert plate (3560) of the present example includes a pair of slots (3564) that are configured to receive a molten plastic material during such an injection molding process, to assist in securing such material to metal insert plate (3560) as the material cools to form outer sheath (3532). It will be appreciated that the presence of metal insert plate (3560) within fin (3555) during the cooling of the material forming outer sheath (3532) may assist in preventing warpage and/or shrinkage of fin (3555) and/or other portions of outer sheath (3532), thereby promoting proper alignment of the ultrasonic blade. In addition, or alternatively, the presence of metal insert plate (3560) within fin (3555) may provide increased mechanical strength to fin (3555) during use, such as by resisting lateral deflection of fin (3555), and/or may more generally strengthen the joint defined between shaft assembly (3530) and the clamp arm assembly. In some instances, metal insert plate (3560) may resist shearing of the plastic material forming outer sheath (3532), and/or may otherwise provide improved robustness to instrument (3500) over multiple uses of instrument (3500).

While metal insert plate (3560) has been described in connection with instrument (3500), it will be appreciated that metal insert plate (3560) may be readily incorporated into any of the instruments described herein, such as any of instruments (3100, 3200, 3300, 3400). For example, metal insert plate (3560) may provide increased mechanical strength to any of fins (3155, 3255, 3355, 3455), and/or may more generally strengthen the joint defined between any of shaft assemblies (3130, 3230, 3330, 3430) and the corresponding clamp arm assembly (3150, 3250, 3350, 3450).

F. Shaft Assembly with Plastic Outer Sheath and Metal Insert Tube

Figure 22:
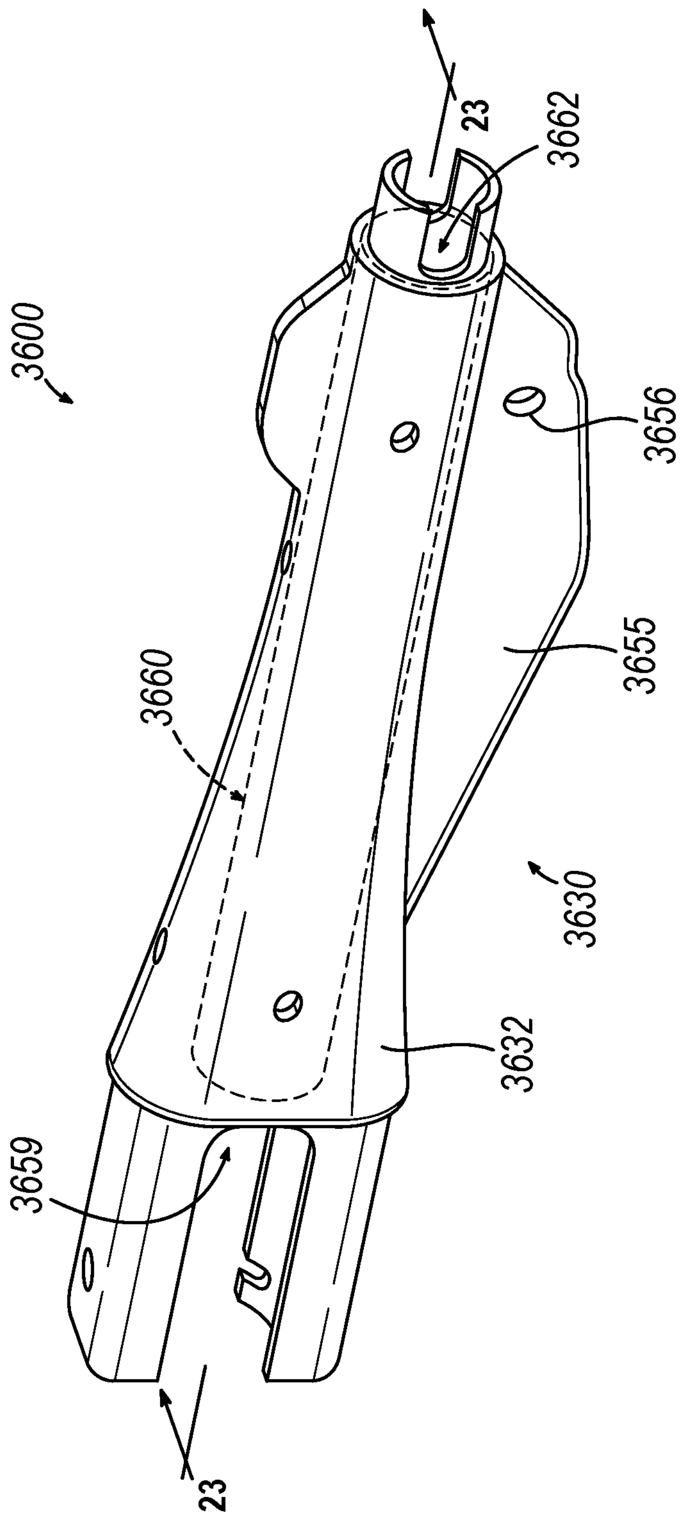
FIG. 22 depicts an enlarged perspective view of another example of a surgical instrument including a clamp arm assembly pivotally coupled to a shaft assembly, and having a metal insert tube disposed within a lumen of the shaft assembly.
Figure 23:
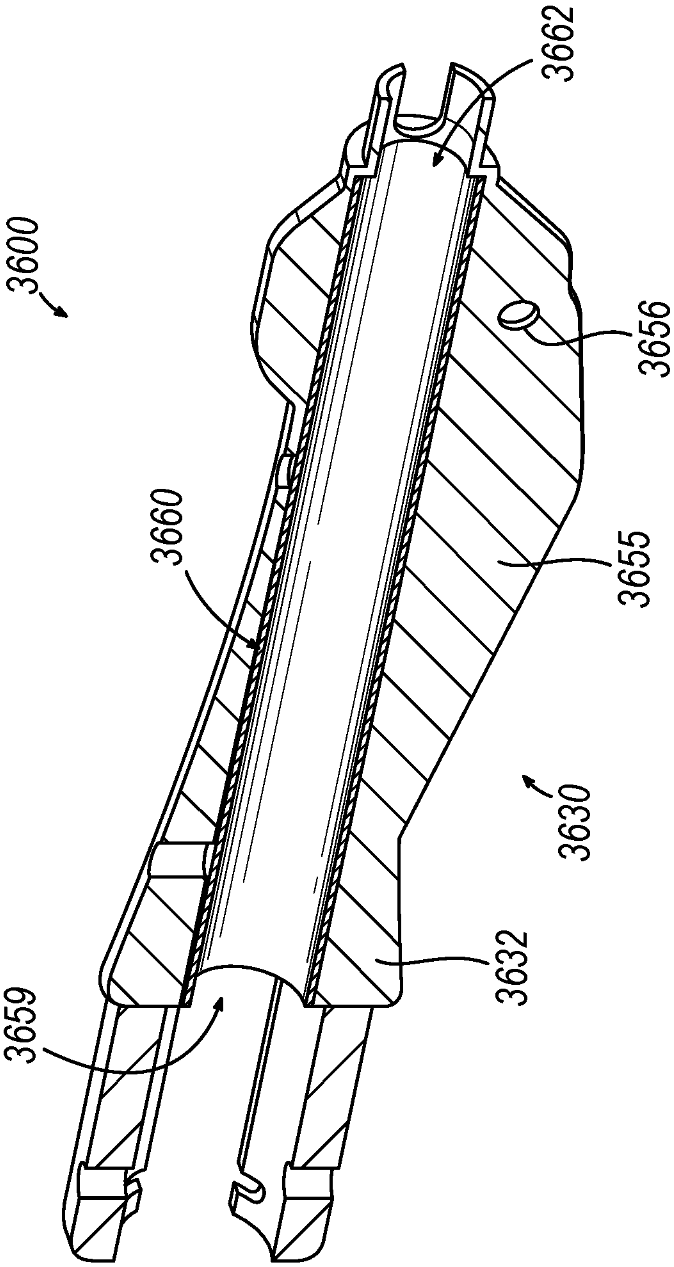
FIG. 23 depicts a perspective sectional view of the shaft assembly of FIG. 22, taken along section line 23-23 of FIG. 22.

FIGS. 22-23 show another example of an ultrasonic surgical instrument (3600) that is operable to cut tissue and seal or weld tissue (e.g., a blood vessel, etc.) substantially simultaneously. Instrument (3600) may be similar to instrument (3400) described above, except as otherwise described below. In this regard, instrument (3600) of this example comprises a handle assembly (not shown) similar to handle assembly (3120), a shaft assembly (3630), and an end effector (not shown) similar to end effector (3440). Instrument (3600) also includes a clamp arm assembly (not shown) similar to clamp arm assembly (3450) that is pivotable toward and away from a body of the handle assembly. Shaft assembly (3630) comprises an outer sheath (also referred to as a "pivot shaft") (3632) extending distally from the body of the handle assembly. A cap (not shown) similar to cap (3434) is secured to the distal end of sheath (3632).

In the example shown, outer sheath (3632) is formed of a plastic material and is configured to be pivotally coupled with the clamp arm assembly. In this regard, outer sheath (3632) of the present example includes a vertically-extending projection (also referred to as a "fin") (3655) and at least one first pivot member in the form of a generally circular receptacle (3656) that extends laterally through fin (3655) and that is configured to securely and pivotally retain at least one second pivot member (e.g., a pair of bosses) of the clamp arm assembly, such as in a manner similar to that described above. For example, the at least one receptacle (3656) may be configured to provide a snap-fit engagement with both bosses, with such a snap-fit engagement permitting rotation of both bosses relative to the at least one receptacle (3656) about a pivot axis collectively defined by the bosses and the at least one receptacle (3656). Outer sheath (3632) of the present example also includes a lumen (3659) configured to receive at least a portion of the acoustic waveguide that communicates ultrasonic vibrations to the ultrasonic blade of the end effector.

In the example shown, shaft assembly (3630) further comprises a metal insert tube (3660) received within lumen (3659) of outer sheath (3632) and having a lumen (3662) configured to be axially aligned with the lumen (3659) of outer sheath (3632), such that lumen (3662) of metal insert tube (3660) may be configured to receive at least a portion of the acoustic waveguide that communicates ultrasonic vibrations to the ultrasonic blade of the end effector. Outer sheath (3632) may be overmolded onto metal insert tube (3660) via an injection molding process. It will be appreciated that the presence of metal insert tube (3660) within lumen (3659) of outer sheath (3632) during the cooling of the material forming outer sheath (3632) may assist in preventing warpage and/or shrinkage of outer sheath (3632), thereby promoting proper alignment of the ultrasonic blade. In addition, or alternatively, the presence of metal insert tube (3660) within lumen (3659) of outer sheath (3632) may provide increased mechanical strength to shaft assembly (3630) during use.

While metal insert tube (3660) has been described in connection with instrument (3600), it will be appreciated that metal insert tube (3660) may be readily incorporated into any of the instruments described herein, such as any of instruments (3100, 3200, 3300, 3400, 3500). For example, metal insert tube (3660) may provide increased mechanical strength to any of shaft assemblies (3130, 3230, 3330, 3430, 3530).

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a body; (b) a shaft assembly extending distally from the body, wherein the shaft assembly includes an outer sheath and a first pivot portion, wherein the outer sheath and the first pivot portion are integrally formed together with each other as a first unitary piece; (c) an ultrasonic blade positioned distal to the shaft assembly; and (d) a clamp arm assembly including a clamp arm and a second pivot portion, wherein the clamp arm and the second pivot portion are integrally formed together with each other as a second unitary piece, wherein the clamp arm assembly is pivotally coupled to the shaft assembly via the first and second pivot portions.

Example 2

The surgical instrument of Example 1, wherein the first pivot portion includes a first pivot member, and wherein the second pivot portion includes a second pivot member.

Example 3

The surgical instrument of Example 2, wherein the first pivot member comprises a first material, wherein the second pivot member comprises a second material different from the first material.

Example 4

The surgical instrument of Example 3, wherein one of the first or second materials comprises a plastic material, wherein the other of the first or second materials comprises a metal material.

Example 5

The surgical instrument of any one or more of Examples 2 through 4, wherein the first pivot member comprises at least one boss, wherein the second pivot member comprises at least one receptacle configured to pivotally receive the at least one boss.

Example 6

The surgical instrument of any one or more of Examples 2 through 5, wherein the second pivot member comprises at least one boss, wherein the first pivot member comprises at least one receptacle configured to pivotally receive the at least one boss.

Example 7

The surgical instrument of any one or more of Examples 2 through 6, wherein the outer sheath includes a fin, wherein the first pivot member is disposed on the fin.

Example 8

The surgical instrument of Example 7, further comprising a metal insert plate disposed within the fin.

Example 9

The surgical instrument of any one or more of Examples 1 through 8, wherein the outer sheath includes a lumen.

Example 10

The surgical instrument of Example 9, further comprising a metal insert tube disposed within the lumen.

Example 11

The surgical instrument of any one or more of Examples 9 through 10, wherein the outer sheath comprises a plastic material.

Example 12

The surgical instrument of any one or more of Examples 1 through 12, wherein the first pivot portion includes a first boss and a second boss, wherein the second pivot portion includes a first receptacle and a second receptacle, and wherein the first and second receptacles respectively receive the first and second bosses.

Example 13

The surgical instrument of Example 12, wherein the outer sheath includes a fin, and wherein the first and second bosses extend from the fin.

Example 14

The surgical instrument of any one or more of Examples 1 through 13, wherein the first pivot portion includes a first receptacle, wherein the second pivot portion includes a first boss, and wherein the first receptacles receives the first boss.

Example 15

The surgical instrument of Example 14, wherein the outer sheath includes a fin, and wherein the fin defines the first receptacle.

Example 16

A surgical instrument, comprising: (a) a body; (b) a shaft assembly extending distally from the body, wherein the shaft assembly includes an outer sheath, an inner tube, and a first pivot portion, wherein the inner tube extends through the outer sheath defining a lumen therethrough; (c) an ultrasonic blade positioned distal to the shaft assembly; and (d) a clamp arm assembly including a clamp arm and a second pivot portion, wherein the clamp arm assembly is pivotally coupled to the shaft assembly via the first and second pivot portions, wherein the outer sheath is formed of a first material, wherein the inner tube is formed of a second material, and wherein the first material is different than the second material.

Example 17

The surgical instrument of Example 16, wherein the outer sheath is overmolded to the inner tube.

Example 18

The surgical instrument of any one or more of Examples 16 through 17, wherein the first material is a plastic material.

Example 19

The surgical instrument of any one or more of Examples 16 through 18, wherein the second material is a metal material.

Example 20

A method of assembling at least a portion of a surgical instrument, the surgical instrument including (a) a body; (b) a shaft assembly extending distally from the body, wherein the shaft assembly includes an outer sheath, an inner tube, and a first pivot portion, wherein the inner tube extends through the outer sheath defining a lumen therethrough; (c) an ultrasonic blade positioned distal to the shaft assembly; and (d) a clamp arm assembly including a clamp arm and a second pivot portion, wherein the clamp arm assembly is pivotally coupled to the shaft assembly via the first and second pivot portions, wherein the outer sheath is formed of a first material, wherein the inner tube is formed of a second material, and wherein the first material is different than the second material, the method comprising: (a) overmolding the outer sheath to the inner tube thereby assembling at least the portion of the surgical instrument.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of any claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 5,817,084, entitled "Remote Center Positioning Device with Flexible Drive," issued Oct. 6, 1998, the disclosure of which is incorporated by reference herein; U.S. Pat. No. 5,878,193, entitled "Automated Endoscope System for Optimal Positioning," issued Mar. 2, 1999, the disclosure of which is incorporated by reference herein; U.S. Pat. No. 6,231,565, entitled "Robotic Arm DLUS for Performing Surgical Tasks," issued May 15, 2001, the disclosure of which is incorporated by reference herein; U.S. Pat. No. 6,783,524, entitled "Robotic Surgical Tool with Ultrasound Cauterizing and Cutting Instrument," issued Aug. 31, 2004, the disclosure of which is incorporated by reference herein; U.S. Pat. No. 6,364,888, entitled "Alignment of Master and Slave in a Minimally Invasive Surgical Apparatus," issued Apr. 2, 2002, the disclosure of which is incorporated by reference herein; U.S. Pat. No. 7,524,320, entitled "Mechanical Actuator Interface System for Robotic Surgical Tools," issued Apr. 28, 2009, the disclosure of which is incorporated by reference herein; U.S. Pat. No. 7,691,098, entitled "Platform Link Wrist Mechanism," issued Apr. 6, 2010, the disclosure of which is incorporated by reference herein; U.S. Pat. No. 7,806,891, entitled "Repositioning and Reorientation of Master/Slave Relationship in Minimally Invasive Telesurgery," issued Oct. 5, 2010, the disclosure of which is incorporated by reference herein; U.S. Pat. No. 8,844,789, entitled "Automated End Effector Component Reloading System for Use with a Robotic System," issued Sep. 30, 2014, the disclosure of which is incorporated by reference herein; U.S. Pat. No. 8,820,605, entitled "Robotically-Controlled Surgical Instruments," issued Sep. 2, 2014, the disclosure of which is incorporated by reference herein; U.S. Pat. No. 8,616,431, entitled "Shiftable Drive Interface for Robotically-Controlled Surgical Tool," issued Dec. 31, 2013, the disclosure of which is incorporated by reference herein; U.S. Pat. No. 8,573,461, entitled "Surgical Stapling Instruments with Cam-Driven Staple Deployment Arrangements," issued Nov. 5, 2013, the disclosure of which is incorporated by reference herein; U.S. Pat. No. 8,602,288, entitled "Robotically-Controlled Motorized Surgical End Effector System with Rotary Actuated Closure Systems Having Variable Actuation Speeds," issued Dec. 10, 2013, the disclosure of which is incorporated by reference herein; U.S. Pat. No. 9,301,759, entitled "Robotically-Controlled Surgical Instrument with Selectively Articulatable End Effector," issued Apr. 5, 2016, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a clinician immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention is understood not to be limited to the details of structure and operation shown and described in the specification and drawings.

We claim:

1. A surgical instrument, comprising:
(a) a body;
(b) a shaft assembly extending distally from the body, wherein the shaft assembly includes an outer sheath and a first pivot portion, wherein the outer sheath and the first pivot portion are integrally formed together with each other as a first unitary piece wherein the outer sheath includes a first lumen, wherein the shaft assembly includes a metal insert tube disposed within the first lumen, wherein the metal insert tube includes a second lumen;
(c) an ultrasonic blade positioned distal to the shaft assembly;
(d) a clamp arm assembly including a clamp arm and a second pivot portion, wherein the clamp arm and the second pivot portion are integrally formed together with each other as a second unitary piece, wherein the clamp arm assembly is pivotally coupled to the shaft assembly via the first and second pivot portions; and
(e) an acoustic waveguide at least partially received within the second lumen,
wherein the second lumen is axially aligned with the first lumen.

2. The surgical instrument of claim 1, wherein the first pivot portion includes a first pivot member, and wherein the second pivot portion includes a second pivot member.

3. The surgical instrument of claim 2, wherein the first pivot member comprises a first material, wherein the second pivot member comprises a second material different from the first material.

4. The surgical instrument of claim 3, wherein one of the first or second materials comprises a plastic material, wherein the other of the first or second materials comprises a metal material.

5. The surgical instrument of claim 2, wherein the first pivot member comprises at least one boss, wherein the second pivot member comprises at least one receptacle configured to pivotally receive the at least one boss.

6. The surgical instrument of claim 2, wherein the second pivot member comprises at least one boss, wherein the first pivot member comprises at least one receptacle configured to pivotally receive the at least one boss.

7. The surgical instrument of claim 2, wherein the outer sheath includes a fin, wherein the first pivot member is disposed on the fin.

8. The surgical instrument of claim 7, further comprising a metal insert plate disposed within the fin.

9. The surgical instrument of claim 1, wherein the outer sheath comprises a plastic material.

10. The surgical instrument of claim 1, wherein the first pivot portion includes a first boss and a second boss, wherein the second pivot portion includes a first receptacle and a second receptacle, and wherein the first and second receptacles respectively receive the first and second bosses.

11. The surgical instrument of claim 10, wherein the outer sheath includes a fin, and wherein the first and second bosses extend from the fin.

12. The surgical instrument of claim 1, wherein the first pivot portion includes a first receptacle, wherein the second pivot portion includes a first boss, and wherein the first receptacles receives the first boss.

13. The surgical instrument of claim 12, wherein the outer sheath includes a fin, and wherein the fin defines the first receptacle.

14. A surgical instrument, comprising:
(a) a body;
(b) a shaft assembly extending distally from the body, wherein the shaft assembly includes an outer sheath, an inner tube, and a first pivot portion, wherein the inner tube extends through the outer sheath defining a lumen therethrough, wherein the outer sheath and the first pivot portion are integrally formed together with each other as a first unitary piece;
(c) an ultrasonic blade positioned distal to the shaft assembly; and (d) a clamp arm assembly including a clamp arm and a second pivot portion, wherein the clamp arm and the second pivot portion are integrally formed together with each other as a second unitary piece, wherein the clamp arm assembly is pivotally coupled to the shaft assembly via the first and second pivot portions, wherein the outer sheath is formed of a first material, wherein the inner tube is formed of a second material, and wherein the first material is different than the second material, wherein the first pivot portion includes a first pivot member, wherein the second pivot portion includes a second pivot member, wherein the outer sheath includes a fin, wherein the first pivot member is disposed on the fin, and wherein the surgical instrument further comprises a metal insert plate disposed within the fin.

15. The surgical instrument of claim 14, wherein the outer sheath is overmolded to the inner tube.

16. The surgical instrument of claim 14, wherein the first material is a plastic material.

17. The surgical instrument of claim 16, wherein the second material is a metal material.

18. A method of assembling at least a portion of a surgical instrument, the surgical instrument including (a) a body; (b) a shaft assembly extending distally from the body, wherein the shaft assembly includes an outer sheath, an inner tube, and a first pivot portion, wherein the inner tube extends through the outer sheath defining a lumen therethrough, and wherein the outer sheath and the first pivot portion are integrally formed together with each other as a first unitary piece; (c) an ultrasonic blade positioned distal to the shaft assembly; and (d) a clamp arm assembly including a clamp arm and a second pivot portion, wherein the clamp arm and the second pivot portion are integrally formed together with each other as a second unitary piece, wherein the clamp arm assembly is pivotally coupled to the shaft assembly via the first and second pivot portions, wherein the first pivot portion includes a first pivot member, wherein the second pivot portion includes a second pivot member, wherein the outer sheath includes a fin, wherein the first pivot member is disposed on the fin, and wherein the surgical instrument further comprises a metal insert plate disposed within the fin, wherein the outer sheath is formed of a first material, wherein the inner tube is formed of a second material, and wherein the first material is different than the second material, the method comprising:

(a) overmolding the outer sheath to the inner tube thereby assembling at least the portion of the surgical instrument.

19. The surgical instrument of claim 1, wherein the first lumen extends along an entire length of the outer sheath.

20. The surgical instrument of claim 14, wherein the lumen extends along an entire length of the outer sheath.

* * * * *